US010758361B2

(12) United States Patent
Blain

(10) Patent No.: US 10,758,361 B2
(45) Date of Patent: Sep. 1, 2020

(54) FACET JOINT IMPLANT

(71) Applicant: Spinal Elements, Inc., Carlsbad, CA (US)

(72) Inventor: Jason Blain, Encinitas, CA (US)

(73) Assignee: Spinal Elements, Inc., Carlsbad, CA (US)

( * ) Notice: Subject to any disclaimer, the term of this patent is extended or adjusted under 35 U.S.C. 154(b) by 0 days.

(21) Appl. No.: 14/995,618

(22) Filed: Jan. 14, 2016

(65) Prior Publication Data

US 2016/0213481 A1   Jul. 28, 2016

Related U.S. Application Data

(60) Provisional application No. 62/108,451, filed on Jan. 27, 2015.

(51) Int. Cl.
*A61F 2/44* (2006.01)
*A61F 2/30* (2006.01)

(52) U.S. Cl.
CPC ...... *A61F 2/4405* (2013.01); *A61F 2002/302* (2013.01); *A61F 2002/30471* (2013.01);
(Continued)

(58) Field of Classification Search
CPC .................. A61B 17/7062; A61B 17/7064
See application file for complete search history.

(56) References Cited

U.S. PATENT DOCUMENTS

| 86,016 A | 1/1869 | Howell |
|---|---|---|
| 1,630,239 A | 5/1927 | Binkley et al. |

(Continued)

FOREIGN PATENT DOCUMENTS

| CA | 1 329 525 | 5/1994 |
|---|---|---|
| CA | 2 437 575 | 4/2009 |

(Continued)

OTHER PUBLICATIONS

3rd Party Lab Notebook, "Facet Cartilage Repair," dated May 20, 2003 in 2 pages.
(Continued)

*Primary Examiner* — Jacqueline T Johanas
(74) *Attorney, Agent, or Firm* — Knobbe, Martens, Olson & Bear, LLP

(57) ABSTRACT

Methods and devices are disclosed for treating the facet joint. An implant for treating the facet joint is provided comprising a fixation plate having an access surface and a bone facing surface, a spacer configured to be inserted into the facet joint, and at least one hinge between the spacer and the bone facing surface of the fixation plate. A method for treating a facet joint comprising a superior articular process and an inferior articular process is provided comprising the steps of implanting a spacer between the superior articular process and the inferior articular process, positioning a fixation plate over the facet joint, and securing the fixation plate to at least one of the superior articular process and the inferior articular process. Another method comprises the steps of providing an implant comprising a fixation plate having an access surface and a bone facing surface, a spacer, and at least one hinge between the spacer and the bone facing surface of the fixation plate.

19 Claims, 15 Drawing Sheets

(52) U.S. Cl.
CPC .............. *A61F 2002/30578* (2013.01); *A61F 2002/30754* (2013.01)

(56) References Cited

U.S. PATENT DOCUMENTS

| | | |
|---|---|---|
| 1,822,280 A | 9/1931 | Ervay |
| 1,822,330 A | 9/1931 | Anslie |
| 1,845,428 A | 2/1932 | Llewellyn |
| 2,440,123 A | 4/1948 | Smith |
| 2,486,303 A | 10/1949 | Longfellow |
| 2,500,993 A | 3/1950 | Christopher |
| 2,677,369 A | 5/1954 | Knowles |
| 2,706,023 A | 4/1955 | Merritt |
| 2,967,282 A | 1/1961 | Schwartz et al. |
| 3,111,945 A | 11/1963 | Von Solbrig |
| 3,149,808 A | 9/1964 | Weckesser |
| 3,426,364 A | 2/1969 | Lumb |
| 3,570,497 A | 3/1971 | Lemole |
| 3,848,601 A | 11/1974 | Ma et al. |
| 3,867,728 A | 2/1975 | Stubstad et al. |
| 3,875,595 A | 4/1975 | Froning |
| 3,879,767 A | 4/1975 | Stubstad |
| 3,893,196 A | 7/1975 | Hochman |
| 3,953,140 A | 4/1976 | Carlstrom |
| 3,987,499 A | 10/1976 | Scharbach et al. |
| 4,001,896 A | 1/1977 | Arkangel |
| 4,013,071 A | 3/1977 | Rosenberg |
| 4,037,603 A | 7/1977 | Wendorff |
| 4,085,466 A | 4/1978 | Goodfellow et al. |
| 4,119,091 A | 10/1978 | Partridge |
| 4,156,296 A | 5/1979 | Johnson et al. |
| 4,164,793 A | 8/1979 | Swanson |
| 4,231,121 A | 11/1980 | Lewis |
| D261,935 S | 11/1981 | Halloran |
| 4,309,777 A | 1/1982 | Patil |
| 4,312,337 A | 1/1982 | Donohue |
| 4,323,217 A | 4/1982 | Dochterman |
| 4,349,921 A | 9/1982 | Kuntz |
| 4,388,921 A | 6/1983 | Sutter et al. |
| 4,401,112 A | 8/1983 | Rezaian |
| 4,464,090 A | 8/1984 | Duran |
| 4,484,570 A | 11/1984 | Sutter et al. |
| 4,502,161 A | 3/1985 | Wall |
| D279,502 S | 7/1985 | Halloran |
| D279,503 S | 7/1985 | Halloran |
| 4,535,764 A | 8/1985 | Ebert |
| 4,554,914 A | 11/1985 | Kapp et al. |
| 4,573,458 A | 3/1986 | Lower |
| 4,573,459 A | 3/1986 | Lower |
| 4,599,086 A | 7/1986 | Doty |
| 4,634,445 A | 1/1987 | Helal |
| 4,662,371 A | 5/1987 | Whipple et al. |
| 4,706,659 A | 11/1987 | Matthews et al. |
| 4,714,469 A | 12/1987 | Kenna |
| 4,722,331 A | 2/1988 | Fox |
| 4,730,615 A | 3/1988 | Sutherland et al. |
| 4,759,766 A | 7/1988 | Buettner-Janz et al. |
| 4,759,769 A | 7/1988 | Hedman et al. |
| 4,772,287 A | 9/1988 | Ray et al. |
| 4,773,402 A | 9/1988 | Asher et al. |
| 4,834,757 A | 5/1989 | Brantigan |
| 4,863,477 A | 9/1989 | Monson |
| 4,892,545 A | 1/1990 | Day et al. |
| 4,904,260 A | 2/1990 | Ray et al. |
| 4,904,261 A | 2/1990 | Dove et al. |
| 4,907,577 A | 3/1990 | Wu |
| 4,911,718 A | 3/1990 | Lee et al. |
| 4,917,704 A | 4/1990 | Frey et al. |
| 4,919,667 A | 4/1990 | Richmond |
| 4,923,471 A | 5/1990 | Morgan |
| 4,936,848 A | 6/1990 | Bagby |
| 4,941,466 A | 7/1990 | Romano |
| 4,955,908 A | 9/1990 | Frey et al. |
| 4,959,065 A | 9/1990 | Arnett et al. |
| 4,969,909 A | 11/1990 | Barouk |
| 5,000,165 A | 3/1991 | Watanabe |
| 5,002,546 A | 3/1991 | Romano |
| 5,002,576 A | 3/1991 | Fuhrmann et al. |
| 5,011,484 A | 4/1991 | Bréard |
| 5,015,255 A | 5/1991 | Kuslich |
| 5,047,055 A | 9/1991 | Bao et al. |
| 5,053,036 A | 10/1991 | Perren et al. |
| 5,057,111 A | 10/1991 | Park |
| 5,062,845 A | 11/1991 | Kuslich |
| 5,071,437 A | 12/1991 | Steffee |
| 5,085,660 A | 2/1992 | Lin |
| 5,092,866 A | 3/1992 | Breard et al. |
| 5,112,013 A | 5/1992 | Tolbert et al. |
| 5,112,346 A | 5/1992 | Hiltebrandt et al. |
| 5,127,912 A | 7/1992 | Ray et al. |
| 5,135,188 A | 8/1992 | Anderson et al. |
| 5,147,361 A | 9/1992 | Ojima et al. |
| 5,147,404 A | 9/1992 | Downey |
| 5,171,280 A | 12/1992 | Baumgartner |
| 5,176,709 A | 1/1993 | Branemark |
| 5,192,326 A | 3/1993 | Bao et al. |
| 5,192,327 A | 3/1993 | Brantigan |
| 5,209,755 A | 5/1993 | Abrahan et al. |
| 5,258,031 A | 11/1993 | Salib et al. |
| 5,269,784 A | 12/1993 | Mast |
| 5,275,601 A | 1/1994 | Gogolewski et al. |
| 5,282,861 A | 2/1994 | Kaplan |
| 5,286,249 A | 2/1994 | Thibodaux |
| 5,300,073 A | 4/1994 | Ray et al. |
| 5,304,179 A | 4/1994 | Wagner |
| 5,306,275 A | 4/1994 | Bryan |
| 5,306,307 A | 4/1994 | Senter et al. |
| 5,306,308 A | 4/1994 | Gross et al. |
| 5,306,309 A | 4/1994 | Wagner et al. |
| 5,326,364 A | 7/1994 | Clift, Jr. et al. |
| 5,330,479 A | 7/1994 | Whitmore |
| 5,360,431 A | 11/1994 | Puno et al. |
| 5,364,399 A | 11/1994 | Lowery et al. |
| 5,368,596 A | 11/1994 | Brookhart |
| 5,370,697 A | 12/1994 | Baumgartner |
| 5,372,598 A | 12/1994 | Luhr et al. |
| 5,397,364 A | 3/1995 | Kozak et al. |
| 5,400,784 A | 3/1995 | Durand et al. |
| 5,401,269 A | 3/1995 | Buttner-Janz et al. |
| 5,413,576 A | 5/1995 | Rivard |
| 5,415,661 A | 5/1995 | Holmes |
| 5,425,773 A | 6/1995 | Boyd et al. |
| 5,437,672 A | 8/1995 | Alleyne |
| 5,445,639 A | 8/1995 | Kuslich et al. |
| 5,458,641 A | 10/1995 | Ramirez Jimenez |
| 5,458,642 A | 10/1995 | Beer et al. |
| 5,458,643 A | 10/1995 | Oka et al. |
| 5,462,542 A | 10/1995 | Alesi, Jr. |
| 5,474,555 A | 12/1995 | Puno et al. |
| 5,487,756 A | 1/1996 | Kallesoe et al. |
| 5,491,882 A | 2/1996 | Walston et al. |
| 5,496,318 A | 3/1996 | Howland et al. |
| 5,501,684 A | 3/1996 | Schlapfer et al. |
| 5,507,823 A | 4/1996 | Walston et al. |
| 5,509,918 A | 4/1996 | Romano |
| 5,514,180 A | 5/1996 | Heggeness et al. |
| 5,520,690 A | 5/1996 | Errico et al. |
| 5,522,899 A | 6/1996 | Michelson |
| 5,527,312 A | 6/1996 | Ray |
| 5,527,314 A | 6/1996 | Brumfield et al. |
| 5,534,027 A | 7/1996 | Hodorek |
| 5,534,028 A | 7/1996 | Bao et al. |
| 5,534,030 A | 7/1996 | Navarro et al. |
| 5,540,706 A | 7/1996 | Aust et al. |
| 5,545,229 A | 8/1996 | Parsons et al. |
| 5,549,619 A | 8/1996 | Peters et al. |
| 5,556,431 A | 9/1996 | Buttner-Janz |
| 5,558,674 A | 9/1996 | Heggeness et al. |
| 5,562,738 A | 10/1996 | Boyd et al. |
| 5,571,105 A | 11/1996 | Gundolf |
| 5,571,131 A | 11/1996 | Ek et al. |
| 5,571,189 A | 11/1996 | Kuslich |
| 5,571,191 A | 11/1996 | Fitz |
| 5,577,995 A | 11/1996 | Walker et al. |

(56) References Cited

U.S. PATENT DOCUMENTS

| | | |
|---|---|---|
| 5,578,034 A | 11/1996 | Estes |
| 5,586,989 A | 12/1996 | Bray, Jr. |
| 5,591,165 A | 1/1997 | Jackson |
| 5,603,713 A | 2/1997 | Aust et al. |
| 5,607,426 A | 3/1997 | Ralph et al. |
| 5,607,428 A | 3/1997 | Lin |
| 5,609,635 A | 3/1997 | Michelson |
| 5,616,144 A | 4/1997 | Yapp et al. |
| 5,638,700 A | 6/1997 | Shechter |
| 5,643,265 A | 7/1997 | Errico et al. |
| 5,645,597 A | 7/1997 | Krapiva |
| 5,645,599 A | 7/1997 | Samani |
| 5,649,947 A | 7/1997 | Auerbach et al. |
| 5,653,762 A | 8/1997 | Pisharodi |
| 5,665,089 A | 9/1997 | Dall et al. |
| 5,674,295 A | 10/1997 | Ray et al. |
| 5,674,296 A | 10/1997 | Bryan et al. |
| 5,676,666 A | 10/1997 | Oxland et al. |
| 5,676,701 A | 10/1997 | Yuan et al. |
| 5,676,702 A | 10/1997 | Ratron |
| 5,681,311 A | 10/1997 | Foley et al. |
| 5,683,464 A | 11/1997 | Wagner et al. |
| 5,683,466 A | 11/1997 | Vitale |
| 5,700,265 A | 12/1997 | Romano |
| 5,702,450 A | 12/1997 | Bisserie |
| 5,707,373 A | 1/1998 | Sevrain et al. |
| 5,713,542 A | 2/1998 | Benoit |
| 5,713,900 A | 2/1998 | Benzel et al. |
| 5,716,415 A | 2/1998 | Steffee |
| 5,725,582 A | 3/1998 | Bevan et al. |
| 5,735,853 A | 4/1998 | Olerud |
| 5,741,260 A | 4/1998 | Songer et al. |
| 5,741,261 A | 4/1998 | Moskovitz et al. |
| 5,743,914 A | 4/1998 | Skiba |
| 5,749,916 A | 5/1998 | Richelsoph |
| 5,755,796 A | 5/1998 | Ibo et al. |
| D395,138 S | 6/1998 | Ohata |
| 5,766,251 A | 6/1998 | Koshino |
| 5,766,253 A | 6/1998 | Brosnahan |
| 5,772,663 A | 6/1998 | Whiteside et al. |
| 5,776,199 A | 7/1998 | Michelson |
| 5,797,916 A | 8/1998 | McDowell |
| 5,807,396 A | 9/1998 | Raveh |
| 5,810,823 A | 9/1998 | Klaue et al. |
| 5,824,093 A | 10/1998 | Ray et al. |
| 5,824,094 A | 10/1998 | Serhan et al. |
| 5,836,948 A | 11/1998 | Zucherman et al. |
| 5,849,004 A | 12/1998 | Bramlet |
| 5,851,207 A | 12/1998 | Cesarone |
| 5,851,208 A | 12/1998 | Trott |
| 5,860,977 A | 1/1999 | Zucherman et al. |
| 5,865,846 A | 2/1999 | Bryan et al. |
| 5,868,745 A | 2/1999 | Alleyne |
| 5,876,402 A | 3/1999 | Errico et al. |
| 5,876,404 A | 3/1999 | Zucherman et al. |
| 5,879,396 A | 3/1999 | Walston et al. |
| 5,888,203 A | 3/1999 | Goldberg |
| 5,888,223 A | 3/1999 | Bray |
| 5,893,889 A | 4/1999 | Harrington |
| 5,895,428 A | 4/1999 | Berry |
| 5,902,303 A | 5/1999 | Eckhof et al. |
| 5,904,683 A | 5/1999 | Pohndorf et al. |
| RE36,221 E | 6/1999 | Breard et al. |
| 5,918,604 A | 7/1999 | Whelan |
| 5,925,048 A | 7/1999 | Ahmad et al. |
| 5,931,838 A | 8/1999 | Vito |
| 5,951,555 A | 9/1999 | Rehak et al. |
| 5,951,558 A | 9/1999 | Fiz |
| 5,954,722 A | 9/1999 | Bono |
| 5,964,765 A | 10/1999 | Fenton et al. |
| 5,993,452 A | 11/1999 | Vandewalle |
| 5,997,542 A | 12/1999 | Burke |
| 6,001,130 A | 12/1999 | Bryan et al. |
| 6,014,588 A | 1/2000 | Fitz |
| 6,019,763 A | 2/2000 | Nakamura et al. |
| 6,019,792 A | 2/2000 | Cauthen |
| 6,030,389 A | 2/2000 | Wagner et al. |
| 6,039,763 A | 3/2000 | Shelokov |
| 6,048,342 A | 4/2000 | Zucherman et al. |
| 6,050,998 A | 4/2000 | Fletcher |
| 6,063,121 A | 5/2000 | Xavier et al. |
| 6,066,175 A | 5/2000 | Henderson et al. |
| 6,066,325 A | 5/2000 | Wallace et al. |
| 6,068,630 A | 5/2000 | Zucherman et al. |
| RE36,758 E | 6/2000 | Fitz |
| 6,080,157 A | 6/2000 | Cathro et al. |
| 6,082,568 A | 7/2000 | Flanagan |
| 6,099,531 A | 8/2000 | Bonutti |
| 6,102,347 A | 8/2000 | Benoit |
| 6,106,558 A | 8/2000 | Picha |
| 6,113,637 A | 9/2000 | Gi, II et al. |
| 6,117,173 A | 9/2000 | Taddia et al. |
| 6,132,464 A | 10/2000 | Martin |
| 6,132,465 A | 10/2000 | Ray et al. |
| 6,136,031 A | 10/2000 | Middleton |
| 6,139,550 A | 10/2000 | Michelson |
| 6,146,422 A | 11/2000 | Lawson |
| 6,152,927 A | 11/2000 | Farris et al. |
| 6,156,037 A | 12/2000 | Le Huec et al. |
| 6,156,067 A | 12/2000 | Bryan et al. |
| 6,179,839 B1 | 1/2001 | Weiss et al. |
| 6,193,721 B1 | 2/2001 | Michelson |
| D439,340 S | 3/2001 | Michelson |
| 6,200,322 B1 | 3/2001 | Branch et al. |
| 6,206,881 B1 | 3/2001 | Frigg et al. |
| 6,231,610 B1 | 5/2001 | Geisler |
| 6,235,033 B1 | 5/2001 | Brace et al. |
| 6,235,034 B1 | 5/2001 | Bray |
| 6,235,059 B1 | 5/2001 | Benezech et al. |
| 6,241,731 B1 | 6/2001 | Fiz |
| 6,261,291 B1 | 7/2001 | Talaber et al. |
| 6,273,889 B1 | 8/2001 | Richelsoph |
| 6,287,309 B1 | 9/2001 | Baccelli et al. |
| 6,293,949 B1 | 9/2001 | Justis et al. |
| 6,302,883 B1 | 10/2001 | Bono |
| 6,306,136 B1 | 10/2001 | Baccelli |
| 6,306,139 B1 | 10/2001 | Fuentes |
| 6,306,170 B2 | 10/2001 | Rau |
| D450,122 S | 11/2001 | Michelson |
| 6,325,803 B1 | 12/2001 | Schumacher et al. |
| 6,331,179 B1 | 12/2001 | Freid et al. |
| 6,342,055 B1 | 1/2002 | Eisermann et al. |
| D454,953 S | 3/2002 | Michelson |
| 6,368,325 B1 | 4/2002 | McKinley et al. |
| 6,368,350 B1 | 4/2002 | Erickson et al. |
| 6,371,958 B1 | 4/2002 | Overaker |
| 6,375,573 B2 | 4/2002 | Romano |
| 6,379,386 B1 | 4/2002 | Resch et al. |
| 6,383,186 B1 | 5/2002 | Michelson |
| 6,395,035 B2 | 5/2002 | Bresina et al. |
| 6,402,755 B1 | 6/2002 | Pisharodi |
| D460,188 S | 7/2002 | Michelson |
| D460,189 S | 7/2002 | Michelson |
| 6,413,259 B1 | 7/2002 | Lyons et al. |
| 6,419,678 B1 | 7/2002 | Asfora |
| 6,419,703 B1 | 7/2002 | Fallin et al. |
| 6,428,542 B1 | 8/2002 | Michelson |
| 6,432,106 B1 | 8/2002 | Fraser |
| 6,436,099 B1 | 8/2002 | Drewry et al. |
| 6,436,101 B1 | 8/2002 | Hamada et al. |
| 6,436,146 B1 | 8/2002 | Hassler et al. |
| D463,560 S | 9/2002 | Michelson |
| 6,447,544 B1 | 9/2002 | Michelson |
| 6,454,769 B2 | 9/2002 | Wagner et al. |
| 6,461,359 B1 | 10/2002 | Tribus et al. |
| 6,470,207 B1 | 10/2002 | Simon et al. |
| 6,503,250 B2 | 1/2003 | Paul |
| 6,508,818 B2 | 1/2003 | Steiner et al. |
| 6,565,570 B2 | 5/2003 | Sterett et al. |
| 6,565,605 B2 | 5/2003 | Goble et al. |
| 6,572,617 B1 | 6/2003 | Senegas |
| 6,575,975 B2 | 6/2003 | Brace et al. |
| 6,579,290 B1 | 6/2003 | Hardcastle et al. |
| 6,579,318 B2 | 6/2003 | Varga et al. |

(56) References Cited

U.S. PATENT DOCUMENTS

| | | |
|---|---|---|
| 6,579,319 B2 | 6/2003 | Goble et al. |
| 6,589,244 B1 | 7/2003 | Sevrain et al. |
| 6,599,290 B2 | 7/2003 | Bailey et al. |
| 6,600,956 B2 | 7/2003 | Maschino et al. |
| 6,602,255 B1 | 8/2003 | Campbell et al. |
| 6,602,256 B1 | 8/2003 | Hayes |
| 6,607,530 B1 | 8/2003 | Carl et al. |
| 6,610,091 B1 | 8/2003 | Reiley |
| D479,331 S | 9/2003 | Pike et al. |
| 6,613,053 B1 | 9/2003 | Collins et al. |
| 6,623,486 B1 | 9/2003 | Weaver et al. |
| 6,626,907 B2 | 9/2003 | Campbell et al. |
| 6,626,911 B1 | 9/2003 | Engman et al. |
| 6,626,944 B1 | 9/2003 | Taylor |
| 6,641,614 B1 | 11/2003 | Wagner et al. |
| 6,645,208 B2 | 11/2003 | Apfelbaum et al. |
| 6,645,209 B2 | 11/2003 | Hall, IV et al. |
| 6,652,525 B1 | 11/2003 | Assaker et al. |
| 6,656,181 B2 | 12/2003 | Dixon et al. |
| 6,656,195 B2 | 12/2003 | Peters et al. |
| 6,669,697 B1 | 12/2003 | Pisharodi |
| 6,669,700 B1 | 12/2003 | Farris et al. |
| 6,669,729 B2 | 12/2003 | Chin |
| 6,682,561 B2 | 1/2004 | Songer et al. |
| 6,682,563 B2 | 1/2004 | Scharf |
| 6,695,845 B2 | 2/2004 | Dixon et al. |
| 6,695,846 B2 | 2/2004 | Richelsoph et al. |
| 6,702,817 B2 | 3/2004 | Beger et al. |
| 6,706,068 B2 | 3/2004 | Ferree |
| 6,730,127 B2 | 5/2004 | Michelson |
| 6,740,087 B2 | 5/2004 | Knox |
| 6,743,232 B2 | 6/2004 | Overaker et al. |
| 6,746,450 B1 | 6/2004 | Wall et al. |
| 6,755,833 B1 | 6/2004 | Paul et al. |
| 6,761,720 B1 | 7/2004 | Senegas |
| 6,764,491 B2 | 7/2004 | Frey et al. |
| 6,770,095 B2 | 8/2004 | Grinberg et al. |
| 6,780,186 B2 | 8/2004 | Errico et al. |
| 6,783,527 B2 | 8/2004 | Drewry et al. |
| 6,790,210 B1 | 9/2004 | Cragg et al. |
| 6,802,867 B2 | 10/2004 | Lawson et al. |
| 6,811,567 B2 | 11/2004 | Reiley |
| 6,833,006 B2 | 12/2004 | Foley et al. |
| 6,835,208 B2 | 12/2004 | Marchosky |
| 6,884,242 B2 | 4/2005 | LeHuec et al. |
| 6,890,334 B2 | 5/2005 | Brace et al. |
| 6,890,335 B2 | 5/2005 | Grabowski et al. |
| 6,902,566 B2 | 6/2005 | Zucherman et al. |
| 6,908,484 B2 | 6/2005 | Zubok et al. |
| 6,962,606 B2 | 11/2005 | Michelson |
| 6,964,664 B2 | 11/2005 | Freid et al. |
| 6,966,930 B2 | 11/2005 | Arnin et al. |
| 6,974,478 B2 | 12/2005 | Reiley et al. |
| 6,974,479 B2 | 12/2005 | Trieu |
| 6,984,234 B2 | 1/2006 | Bray |
| 7,001,389 B1 | 2/2006 | Navarro et al. |
| D517,404 S | 3/2006 | Schluter |
| 7,008,429 B2 | 3/2006 | Golobek |
| 7,013,675 B2 | 3/2006 | Marquez-Pickering |
| 7,025,769 B1 | 4/2006 | Ferree |
| 7,048,739 B2 | 5/2006 | Konieczynski et al. |
| 7,051,451 B2 | 5/2006 | Augostino et al. |
| 7,063,701 B2 | 6/2006 | Michelson |
| 7,074,238 B2 | 7/2006 | Stinson et al. |
| 7,077,844 B2 | 7/2006 | Michelson |
| 7,101,375 B2 | 9/2006 | Zucherman et al. |
| 7,112,222 B2 | 9/2006 | Fraser et al. |
| 7,135,024 B2 | 11/2006 | Cook et al. |
| 7,172,627 B2 | 2/2007 | Fiere et al. |
| 7,186,254 B2 | 3/2007 | Dinh et al. |
| 7,220,263 B2 | 5/2007 | Cordaro |
| 7,223,269 B2 | 5/2007 | Chappuis |
| 7,232,464 B2 | 6/2007 | Mathieu et al. |
| 7,273,481 B2 | 9/2007 | Lombardo et al. |
| 7,306,605 B2 | 12/2007 | Ross |
| 7,309,340 B2 | 12/2007 | Fallin et al. |
| D565,180 S | 3/2008 | Liao |
| 7,371,238 B2 | 5/2008 | Sololeski et al. |
| 7,458,981 B2 | 12/2008 | Fielding et al. |
| 7,481,829 B2 | 1/2009 | Baynham et al. |
| 7,481,830 B2 | 1/2009 | Wall et al. |
| 7,517,358 B2 | 4/2009 | Petersen |
| 7,524,325 B2 | 4/2009 | Khalili |
| 7,537,611 B2 | 5/2009 | Lee |
| 7,547,324 B2 | 6/2009 | Cragg et al. |
| 7,559,940 B2 | 7/2009 | McGuire et al. |
| 7,563,286 B2 | 7/2009 | Gerber et al. |
| 7,585,300 B2 | 9/2009 | Cha |
| 7,608,104 B2 | 10/2009 | Yuan et al. |
| 7,621,943 B2 | 11/2009 | Michelson |
| 7,628,816 B2 | 12/2009 | Magerl et al. |
| 7,641,665 B2 | 1/2010 | Zubok et al. |
| 7,651,517 B2 | 1/2010 | Konieczynski et al. |
| 7,693,981 B2 | 4/2010 | Clubb et al. |
| 7,695,472 B2 | 4/2010 | Young |
| 7,799,077 B2 | 9/2010 | Lang et al. |
| 7,806,895 B2 | 10/2010 | Weier et al. |
| 7,819,903 B2 | 10/2010 | Fraser et al. |
| 7,846,183 B2 | 12/2010 | Blain |
| 7,857,839 B2 | 12/2010 | Duong et al. |
| 7,862,590 B2 | 1/2011 | Lim et al. |
| 7,914,561 B2 | 3/2011 | Konieczynski et al. |
| 7,931,840 B2 | 4/2011 | Michelson |
| 7,935,136 B2 | 5/2011 | Alamin et al. |
| 7,935,137 B2 | 5/2011 | Gorhan et al. |
| 7,963,981 B2 | 6/2011 | Binder et al. |
| 7,972,366 B2 | 7/2011 | Richelsoph et al. |
| 7,985,255 B2 | 7/2011 | Bray et al. |
| D643,121 S | 8/2011 | Milford et al. |
| 7,993,370 B2 | 8/2011 | Jahng |
| 7,998,172 B2 | 8/2011 | Blain |
| 8,052,728 B2 | 11/2011 | Hestad |
| 8,100,955 B2 | 1/2012 | Blain et al. |
| 8,109,971 B2 | 2/2012 | Hale |
| 8,133,225 B2 | 3/2012 | Pieske |
| 8,163,016 B2 | 4/2012 | Linares |
| 8,172,877 B2 | 5/2012 | Winslow et al. |
| 8,177,810 B2 | 5/2012 | Ferree |
| 8,192,468 B2 | 6/2012 | Biedermann et al. |
| 8,216,275 B2 | 7/2012 | Fielding et al. |
| 8,231,661 B2* | 7/2012 | Carls ............... A61B 17/7064 606/104 |
| 8,246,655 B2 | 8/2012 | Jackson et al. |
| 8,267,966 B2* | 9/2012 | McCormack ......... A61B 17/025 606/247 |
| 8,268,001 B2 | 9/2012 | Butler et al. |
| 8,282,675 B2 | 10/2012 | Maguire et al. |
| 8,292,954 B2 | 10/2012 | Robinson et al. |
| 8,306,307 B2 | 11/2012 | Koike et al. |
| 8,382,801 B2 | 2/2013 | Lamborne et al. |
| 8,394,125 B2 | 3/2013 | Assell |
| 8,460,346 B2 | 6/2013 | Ralph et al. |
| 8,470,039 B2 | 6/2013 | Blain |
| 8,486,078 B2 | 7/2013 | Carl et al. |
| 8,496,691 B2 | 7/2013 | Blain |
| 8,496,708 B2 | 7/2013 | Blain |
| 8,579,903 B2 | 11/2013 | Carl |
| 8,652,137 B2 | 2/2014 | Blain et al. |
| 8,696,721 B2 | 4/2014 | Blain |
| 8,740,942 B2 | 6/2014 | Blain |
| 8,740,949 B2 | 6/2014 | Blain |
| 8,753,345 B2 | 6/2014 | McCormack et al. |
| 8,784,423 B2 | 7/2014 | Kowarsch et al. |
| 8,801,794 B2 | 8/2014 | Blain |
| 8,858,597 B2 | 10/2014 | Blain |
| 8,882,804 B2 | 11/2014 | Blain |
| 8,961,613 B2 | 2/2015 | Assell et al. |
| D724,733 S | 3/2015 | Blain et al. |
| 8,974,456 B2 | 3/2015 | Allen et al. |
| 8,979,529 B2 | 3/2015 | Marcus |
| 8,992,533 B2 | 3/2015 | Blain et al. |
| 8,998,953 B2 | 4/2015 | Blain |
| 9,017,389 B2 | 4/2015 | Assell et al. |
| 9,060,787 B2 | 6/2015 | Blain et al. |

(56) References Cited

U.S. PATENT DOCUMENTS

| | | | |
|---|---|---|---|
| 9,101,410 B1* | 8/2015 | Urrea | A61B 17/7064 |
| D739,935 S | 9/2015 | Blain et al. | |
| 9,149,283 B2 | 10/2015 | Assell et al. | |
| 9,161,763 B2 | 10/2015 | Assell et al. | |
| 9,179,943 B2 | 11/2015 | Blain | |
| 9,220,547 B2 | 12/2015 | Blain et al. | |
| D748,262 S | 1/2016 | Blain | |
| 9,233,006 B2 | 1/2016 | Assell et al. | |
| D748,793 S | 2/2016 | Blain | |
| 9,265,546 B2 | 2/2016 | Blain | |
| 9,271,765 B2 | 3/2016 | Blain | |
| 9,301,786 B2 | 4/2016 | Blain | |
| 9,314,277 B2 | 4/2016 | Assell et al. | |
| 9,345,488 B2 | 5/2016 | Assell et al. | |
| 9,421,044 B2 | 8/2016 | Blain et al. | |
| 9,427,328 B2 | 8/2016 | Drochner et al. | |
| D765,853 S | 9/2016 | Blain et al. | |
| D765,854 S | 9/2016 | Blain et al. | |
| 9,456,855 B2 | 10/2016 | Blain et al. | |
| 9,517,077 B2 | 12/2016 | Blain et al. | |
| D777,921 S | 1/2017 | Blain et al. | |
| D780,315 S | 2/2017 | Blain et al. | |
| 9,572,602 B2 | 2/2017 | Blain et al. | |
| 9,585,707 B2 | 3/2017 | Blain | |
| 9,615,861 B2 | 4/2017 | Perez-Cruet et al. | |
| D790,062 S | 6/2017 | Blain et al. | |
| 9,675,387 B2 | 6/2017 | Blain | |
| 9,743,937 B2 | 8/2017 | Blain et al. | |
| 9,757,247 B2 | 9/2017 | Mantri | |
| 9,808,294 B2 | 11/2017 | Blain | |
| 9,820,784 B2 | 11/2017 | Blain et al. | |
| 9,839,450 B2 | 12/2017 | Blain et al. | |
| D810,942 S | 2/2018 | Blain et al. | |
| 9,889,020 B2 | 2/2018 | Baynham | |
| D812,754 S | 3/2018 | Blain et al. | |
| 9,936,984 B2 | 4/2018 | Blain | |
| 9,980,825 B2 | 5/2018 | Nichols et al. | |
| 10,022,161 B2 | 7/2018 | Blain | |
| 10,085,776 B2 | 10/2018 | Blain | |
| D834,194 S | 11/2018 | Blain et al. | |
| 10,194,955 B2 | 2/2019 | Blain et al. | |
| 10,251,679 B2 | 4/2019 | Blain et al. | |
| 10,299,938 B1 | 5/2019 | Ehteshami | |
| D857,900 S | 8/2019 | Blain et al. | |
| 10,368,921 B2 | 8/2019 | Blain | |
| 10,426,524 B2 | 10/2019 | Blain | |
| 10,568,664 B2 | 2/2020 | Blain et al. | |
| 2001/0007941 A1 | 7/2001 | Steiner et al. | |
| 2001/0014807 A1 | 8/2001 | Wagner et al. | |
| 2001/0018614 A1 | 8/2001 | Bianchi | |
| 2002/0004683 A1 | 1/2002 | Michelson | |
| 2002/0016595 A1 | 2/2002 | Michelson | |
| 2002/0018799 A1 | 2/2002 | Spector et al. | |
| 2002/0019637 A1 | 2/2002 | Frey et al. | |
| 2002/0022843 A1 | 2/2002 | Michelson | |
| 2002/0029039 A1 | 3/2002 | Zucherman et al. | |
| 2002/0040227 A1 | 4/2002 | Harari | |
| 2002/0045898 A1 | 4/2002 | Freid et al. | |
| 2002/0065557 A1 | 5/2002 | Goble et al. | |
| 2002/0072800 A1 | 6/2002 | Goble et al. | |
| 2002/0077700 A1 | 6/2002 | Varga et al. | |
| 2002/0086047 A1 | 7/2002 | Mueller et al. | |
| 2002/0120335 A1 | 8/2002 | Angelucci et al. | |
| 2002/0123806 A1 | 9/2002 | Reiley | |
| 2002/0147450 A1 | 10/2002 | LeHuec et al. | |
| 2002/0151895 A1* | 10/2002 | Soboleski | A61B 17/7064 606/247 |
| 2002/0169508 A1 | 11/2002 | Songer et al. | |
| 2002/0173800 A1 | 11/2002 | Dreyfuss et al. | |
| 2002/0173813 A1 | 11/2002 | Peterson et al. | |
| 2002/0198527 A1 | 12/2002 | Muckter | |
| 2003/0004572 A1 | 1/2003 | Goble et al. | |
| 2003/0028250 A1 | 2/2003 | Reiley et al. | |
| 2003/0040797 A1 | 2/2003 | Fallin et al. | |
| 2003/0093082 A1 | 5/2003 | Campbell et al. | |
| 2003/0120343 A1 | 6/2003 | Whelan | |
| 2003/0167091 A1 | 9/2003 | Scharf | |
| 2003/0171753 A1 | 9/2003 | Collins et al. | |
| 2003/0176919 A1 | 9/2003 | Schmieding | |
| 2003/0176922 A1 | 9/2003 | Lawson et al. | |
| 2003/0187442 A1 | 10/2003 | Richelsoph et al. | |
| 2003/0187454 A1 | 10/2003 | Gill et al. | |
| 2003/0191532 A1 | 10/2003 | Goble et al. | |
| 2003/0204259 A1 | 10/2003 | Goble et al. | |
| 2003/0212399 A1 | 11/2003 | Dinh et al. | |
| 2003/0216669 A1 | 11/2003 | Lang et al. | |
| 2003/0233146 A1 | 12/2003 | Grinberg et al. | |
| 2004/0006391 A1 | 1/2004 | Reiley | |
| 2004/0010254 A1 | 1/2004 | Cook et al. | |
| 2004/0010318 A1 | 1/2004 | Ferree | |
| 2004/0024462 A1 | 2/2004 | Ferree et al. | |
| 2004/0049271 A1 | 3/2004 | Biedermann et al. | |
| 2004/0049272 A1 | 3/2004 | Reiley | |
| 2004/0049273 A1 | 3/2004 | Reiley | |
| 2004/0049274 A1 | 3/2004 | Reiley | |
| 2004/0049275 A1 | 3/2004 | Reiley | |
| 2004/0049276 A1 | 3/2004 | Reiley | |
| 2004/0049277 A1 | 3/2004 | Reiley | |
| 2004/0049278 A1 | 3/2004 | Reiley | |
| 2004/0049281 A1 | 3/2004 | Reiley | |
| 2004/0059429 A1 | 3/2004 | Amin et al. | |
| 2004/0068319 A1 | 4/2004 | Cordaro | |
| 2004/0087951 A1 | 5/2004 | Khalili | |
| 2004/0087954 A1 | 5/2004 | Allen et al. | |
| 2004/0097935 A1 | 5/2004 | Richelsoph et al. | |
| 2004/0116927 A1 | 6/2004 | Graf | |
| 2004/0127900 A1 | 7/2004 | Konieczynski et al. | |
| 2004/0127904 A1 | 7/2004 | Konieczynski et al. | |
| 2004/0127989 A1 | 7/2004 | Dooris et al. | |
| 2004/0143264 A1 | 7/2004 | McAfee | |
| 2004/0176778 A1 | 9/2004 | Zubok et al. | |
| 2004/0176844 A1 | 9/2004 | Zubok et al. | |
| 2004/0181227 A1 | 9/2004 | Khalili | |
| 2004/0199166 A1 | 10/2004 | Schmieding et al. | |
| 2004/0210219 A1 | 10/2004 | Bray | |
| 2004/0215341 A1 | 10/2004 | Sybert et al. | |
| 2004/0220570 A1 | 11/2004 | Frigg et al. | |
| 2004/0230192 A1 | 11/2004 | Graf | |
| 2004/0230201 A1 | 11/2004 | Yuan et al. | |
| 2004/0230304 A1 | 11/2004 | Yuan et al. | |
| 2004/0260306 A1 | 12/2004 | Fallin et al. | |
| 2005/0010291 A1 | 1/2005 | Stinson et al. | |
| 2005/0015146 A1 | 1/2005 | Louis et al. | |
| 2005/0027296 A1 | 2/2005 | Thramann et al. | |
| 2005/0033433 A1 | 2/2005 | Michelson | |
| 2005/0043797 A1 | 2/2005 | Lee | |
| 2005/0043799 A1 | 2/2005 | Reiley | |
| 2005/0049593 A1 | 3/2005 | Duong et al. | |
| 2005/0049705 A1 | 3/2005 | Hale et al. | |
| 2005/0055096 A1 | 3/2005 | Serh an et al. | |
| 2005/0059972 A1 | 3/2005 | Biscup | |
| 2005/0085913 A1 | 4/2005 | Fraser et al. | |
| 2005/0101960 A1 | 5/2005 | Fiere et al. | |
| 2005/0277933 A1 | 5/2005 | Wall et al. | |
| 2005/0131409 A1 | 6/2005 | Chervitz et al. | |
| 2005/0131538 A1 | 6/2005 | Chervitz et al. | |
| 2005/0143818 A1 | 6/2005 | Yuan et al. | |
| 2005/0149191 A1 | 7/2005 | Cragg et al. | |
| 2005/0159746 A1* | 7/2005 | Grob | A61B 17/1671 606/247 |
| 2005/0177245 A1 | 8/2005 | Leatherbury et al. | |
| 2005/0192576 A1 | 9/2005 | Michelson | |
| 2005/0197700 A1 | 9/2005 | Boehem et al. | |
| 2005/0216017 A1 | 9/2005 | Fielding et al. | |
| 2005/0240201 A1 | 10/2005 | Yeung | |
| 2005/0251256 A1 | 11/2005 | Reiley | |
| 2005/0256494 A1 | 11/2005 | Datta | |
| 2006/0004367 A1 | 1/2006 | Alamin et al. | |
| 2006/0036323 A1 | 2/2006 | Carl et al. | |
| 2006/0041311 A1 | 2/2006 | McLeer | |
| 2006/0084985 A1 | 4/2006 | Kim | |
| 2006/0085006 A1 | 4/2006 | Ek et al. | |
| 2006/0085072 A1 | 4/2006 | Funk et al. | |
| 2006/0111782 A1 | 5/2006 | Petersen | |

(56) References Cited

U.S. PATENT DOCUMENTS

| | | | |
|---|---|---|---|
| 2006/0116684 A1 | 6/2006 | Whelan | |
| 2006/0122604 A1 | 6/2006 | Gorhan et al. | |
| 2006/0149375 A1 | 7/2006 | Yuan et al. | |
| 2006/0200137 A1 | 9/2006 | Soboleski et al. | |
| 2006/0200147 A1 | 9/2006 | Ensign et al. | |
| 2006/0235403 A1 | 10/2006 | Blain | |
| 2006/0235409 A1 | 10/2006 | Blain | |
| 2006/0235418 A1 | 10/2006 | Gil et al. | |
| 2006/0241597 A1* | 10/2006 | Mitchell | A61F 2/4405 606/247 |
| 2006/0241601 A1 | 10/2006 | Trautwein et al. | |
| 2006/0241616 A1 | 10/2006 | Konieczynski et al. | |
| 2006/0241758 A1 | 10/2006 | Peterman et al. | |
| 2006/0247650 A1* | 11/2006 | Yerby | A61B 17/025 606/90 |
| 2006/0293691 A1 | 12/2006 | Mitra et al. | |
| 2007/0055236 A1 | 3/2007 | Hudgins et al. | |
| 2007/0055252 A1 | 3/2007 | Blain et al. | |
| 2007/0055373 A1* | 3/2007 | Hudgins | A61B 17/7064 623/17.11 |
| 2007/0078464 A1 | 4/2007 | Jones et al. | |
| 2007/0100452 A1 | 5/2007 | Prosser | |
| 2007/0118218 A1 | 5/2007 | Hooper | |
| 2007/0123863 A1* | 5/2007 | Winslow | A61B 17/025 606/279 |
| 2007/0135814 A1* | 6/2007 | Farris | A61B 17/7064 606/279 |
| 2007/0149976 A1 | 6/2007 | Hale et al. | |
| 2007/0179619 A1 | 8/2007 | Grab | |
| 2007/0213820 A1 | 9/2007 | Magerl et al. | |
| 2007/0250166 A1* | 10/2007 | McKay | A61B 17/7064 623/17.11 |
| 2007/0270812 A1 | 11/2007 | Peckham | |
| 2008/0009866 A1 | 1/2008 | Alamin et al. | |
| 2008/0058929 A1 | 3/2008 | Whelan | |
| 2008/0103598 A1 | 5/2008 | Trudeau et al. | |
| 2008/0161925 A1 | 7/2008 | Brittan et al. | |
| 2008/0167686 A1 | 7/2008 | Trieu et al. | |
| 2008/0177264 A1 | 7/2008 | Alamin et al. | |
| 2008/0177326 A1 | 7/2008 | Thompson | |
| 2008/0177390 A1 | 7/2008 | Mitchell et al. | |
| 2008/0183211 A1 | 7/2008 | Lamborne et al. | |
| 2008/0208249 A1* | 8/2008 | Blain | A61B 17/1608 606/207 |
| 2008/0228225 A1 | 9/2008 | Trautwein et al. | |
| 2008/0262549 A1 | 10/2008 | Bennett et al. | |
| 2008/0287996 A1 | 11/2008 | Soholeski et al. | |
| 2009/0005818 A1 | 1/2009 | Chin et al. | |
| 2009/0005873 A1 | 1/2009 | Slivka et al. | |
| 2009/0018662 A1 | 1/2009 | Pasquet et al. | |
| 2009/0024166 A1 | 1/2009 | Carl et al. | |
| 2009/0072006 A1 | 3/2009 | Clauson et al. | |
| 2009/0076617 A1 | 3/2009 | Ralph et al. | |
| 2009/0105766 A1 | 4/2009 | Thompson et al. | |
| 2009/0125066 A1 | 5/2009 | Kraus et al. | |
| 2009/0138048 A1 | 5/2009 | Baccelli et al. | |
| 2009/0171360 A1 | 7/2009 | Whelan | |
| 2009/0198282 A1 | 8/2009 | Fielding et al. | |
| 2009/0248077 A1 | 10/2009 | Johns | |
| 2009/0264928 A1 | 10/2009 | Blain | |
| 2009/0264929 A1 | 10/2009 | Alamin et al. | |
| 2009/0270918 A1 | 10/2009 | Attia et al. | |
| 2009/0270929 A1* | 10/2009 | Suddaby | A61B 17/1637 606/324 |
| 2009/0306671 A1* | 12/2009 | McCormack | A61B 17/025 606/90 |
| 2009/0306716 A1 | 12/2009 | Beger et al. | |
| 2009/0326589 A1 | 12/2009 | Lemoine et al. | |
| 2010/0010548 A1 | 1/2010 | Hermida Ochoa | |
| 2010/0070037 A1 | 3/2010 | Parry et al. | |
| 2010/0076503 A1 | 3/2010 | Beyar et al. | |
| 2010/0131008 A1 | 5/2010 | Overes et al. | |
| 2010/0179553 A1 | 7/2010 | Ralph et al. | |
| 2010/0185241 A1 | 7/2010 | Malandain et al. | |
| 2010/0191286 A1 | 7/2010 | Butler | |
| 2010/0204700 A1 | 8/2010 | Falahee | |
| 2010/0204732 A1 | 8/2010 | Alamin et al. | |
| 2010/0234894 A1 | 9/2010 | Alamin et al. | |
| 2010/0249937 A1* | 9/2010 | Blain | A61B 17/7059 623/17.16 |
| 2010/0274289 A1 | 10/2010 | Carls et al. | |
| 2010/0298829 A1 | 11/2010 | Schaller et al. | |
| 2010/0318133 A1 | 12/2010 | Tornier | |
| 2011/0015744 A1* | 1/2011 | Squires | A61F 2/442 623/17.16 |
| 2011/0022050 A1 | 1/2011 | McClellan et al. | |
| 2011/0022089 A1* | 1/2011 | Assell | A61F 2/4405 606/247 |
| 2011/0034956 A1 | 2/2011 | Mazda et al. | |
| 2011/0098816 A1 | 4/2011 | Jacob et al. | |
| 2011/0153020 A1 | 6/2011 | Abdelgany et al. | |
| 2011/0160772 A1 | 6/2011 | Arcenio et al. | |
| 2011/0172712 A1 | 7/2011 | Chee et al. | |
| 2011/0245875 A1 | 10/2011 | Karim | |
| 2011/0295318 A1 | 12/2011 | Alamin et al. | |
| 2011/0301644 A1 | 12/2011 | Belliard | |
| 2012/0016480 A1 | 1/2012 | Gerber et al. | |
| 2012/0022591 A1 | 1/2012 | Baccelli et al. | |
| 2012/0035658 A1 | 2/2012 | Goble et al. | |
| 2012/0041441 A1 | 2/2012 | Bernstein et al. | |
| 2012/0046749 A1 | 2/2012 | Tatsumi | |
| 2012/0101502 A1 | 4/2012 | Kartalian et al. | |
| 2012/0150231 A1 | 6/2012 | Alamin et al. | |
| 2012/0221048 A1 | 8/2012 | Blain | |
| 2012/0221049 A1* | 8/2012 | Blain | A61B 17/7053 606/247 |
| 2012/0221060 A1 | 8/2012 | Blain | |
| 2012/0245586 A1 | 9/2012 | Lehenkari et al. | |
| 2012/0271354 A1 | 10/2012 | Baccelli et al. | |
| 2012/0277801 A1* | 11/2012 | Marik | A61B 17/7064 606/279 |
| 2013/0023878 A1 | 1/2013 | Belliard et al. | |
| 2013/0041410 A1 | 2/2013 | Hestad et al. | |
| 2013/0079778 A1 | 3/2013 | Azuero et al. | |
| 2013/0110238 A1 | 5/2013 | Lindemann et al. | |
| 2013/0123923 A1* | 5/2013 | Pavlov | A61F 2/4455 623/17.16 |
| 2013/0181015 A1 | 7/2013 | Cason | |
| 2013/0197643 A1 | 8/2013 | Greenberg et al. | |
| 2013/0253590 A1* | 9/2013 | Blain | A61B 17/7059 606/279 |
| 2013/0253649 A1 | 9/2013 | Davis | |
| 2013/0261625 A1 | 10/2013 | Koch et al. | |
| 2013/0297024 A1 | 11/2013 | Khurana | |
| 2013/0325065 A1 | 12/2013 | Malandain et al. | |
| 2014/0012318 A1* | 1/2014 | Goel | A61B 17/7064 606/247 |
| 2014/0066758 A1* | 3/2014 | Marik | A61B 17/7064 600/431 |
| 2014/0257397 A1 | 9/2014 | Akbarnia et al. | |
| 2014/0277142 A1 | 9/2014 | Blain | |
| 2014/0277148 A1 | 9/2014 | Blain | |
| 2014/0277149 A1 | 9/2014 | Rooney et al. | |
| 2014/0336653 A1 | 11/2014 | Bromer | |
| 2014/0336768 A1 | 11/2014 | Blain | |
| 2014/0378976 A1 | 12/2014 | Garcia | |
| 2015/0081023 A1 | 3/2015 | Blain | |
| 2015/0094766 A1 | 4/2015 | Blain et al. | |
| 2015/0094767 A1 | 4/2015 | Blain et al. | |
| 2015/0119988 A1 | 4/2015 | Assell et al. | |
| 2015/0164516 A1 | 6/2015 | Blain et al. | |
| 2015/0164652 A1 | 6/2015 | Assell et al. | |
| 2015/0173917 A1 | 6/2015 | Radcliffe et al. | |
| 2015/0190149 A1 | 7/2015 | Assell et al. | |
| 2015/0196330 A1 | 7/2015 | Blain | |
| 2015/0209096 A1 | 7/2015 | Gephart | |
| 2015/0257770 A1 | 9/2015 | Assell et al. | |
| 2015/0257773 A1 | 9/2015 | Blain | |
| 2015/0327872 A1 | 11/2015 | Assell et al. | |
| 2015/0342648 A1* | 12/2015 | McCormack | A61B 17/7002 606/247 |
| 2016/0022438 A1 | 1/2016 | Lamborne et al. | |

(56) References Cited

U.S. PATENT DOCUMENTS

| | | |
|---|---|---|
| 2016/0058481 A1 | 3/2016 | Blain et al. |
| 2016/0113692 A1 | 4/2016 | Knoepfle |
| 2016/0128838 A1 | 5/2016 | Assell et al. |
| 2016/0213481 A1* | 7/2016 | Blain .................. A61F 2/4405 |
| 2016/0324549 A1 | 11/2016 | Blain |
| 2017/0000527 A1 | 1/2017 | Blain et al. |
| 2017/0105767 A1 | 4/2017 | Blain |
| 2017/0189077 A1 | 7/2017 | Blain |
| 2017/0239060 A1 | 8/2017 | Blain |
| 2017/0281232 A1 | 10/2017 | Smith |
| 2018/0014947 A1 | 1/2018 | Baynham |
| 2018/0049780 A1 | 2/2018 | Blain |
| 2018/0085148 A1 | 3/2018 | Blain |
| 2018/0085149 A1 | 3/2018 | Blain |
| 2019/0142478 A1 | 5/2019 | Blain |
| 2019/0192194 A1 | 6/2019 | Blain |
| 2019/0328428 A1 | 10/2019 | Blain |

FOREIGN PATENT DOCUMENTS

| | | |
|---|---|---|
| DE | 30 27 138 | 12/1981 |
| DE | 30 27 148 | 12/1981 |
| DE | 93 04 368 | 5/1993 |
| DE | 297 01 099 | 4/1997 |
| DE | 197 02 201 | 8/1998 |
| DE | 201 12 123 | 9/2001 |
| DE | 101 35 771 | 2/2003 |
| DE | 20 2004 015 912 | 12/2004 |
| EP | 0 238 219 | 9/1987 |
| EP | 0 242 842 | 10/1987 |
| EP | 0 322 334 | 6/1989 |
| EP | 0 392 124 | 10/1990 |
| EP | 0 610 837 | 8/1994 |
| EP | 0 928 603 | 7/1999 |
| EP | 0 974 319 | 1/2000 |
| EP | 1 201 202 | 5/2002 |
| EP | 1 201 256 | 5/2002 |
| EP | 1 346 697 | 9/2003 |
| EP | 1 470 803 | 10/2004 |
| EP | 2 138 122 | 12/2009 |
| EP | 2 822 482 | 1/2015 |
| EP | 2 919 717 | 9/2015 |
| FR | 2 704 745 | 11/1994 |
| FR | 2 722 980 | 2/1996 |
| FR | 2 766 353 | 1/1999 |
| FR | 2 813 519 | 3/2002 |
| FR | 2 859 904 | 3/2005 |
| GB | 2 366 736 | 3/2002 |
| JP | 53-005889 | 1/1978 |
| JP | 62-270147 | 11/1987 |
| JP | 03-100154 | 4/1991 |
| JP | 03-240660 | 10/1991 |
| JP | 08-509918 | 10/1996 |
| JP | 10-179622 | 7/1998 |
| JP | 2000-201941 | 7/2000 |
| JP | 2000-210297 | 8/2000 |
| JP | 2002-515287 | 5/2002 |
| JP | 2003-079649 | 3/2003 |
| JP | 2003-518977 | 6/2003 |
| JP | 2004-500156 | 1/2004 |
| JP | 2004-508888 | 3/2004 |
| JP | 2004-181236 | 7/2004 |
| JP | 2006-230722 | 9/2006 |
| JP | 2006-528540 | 12/2006 |
| JP | 2007-503884 | 3/2007 |
| JP | 2007-517627 | 7/2007 |
| JP | 2007-190389 | 8/2007 |
| JP | 2008-510526 | 4/2008 |
| JP | 2008-522787 | 7/2008 |
| JP | 2008-537498 | 9/2008 |
| JP | 2009-533167 | 9/2009 |
| JP | 2010-510852 | 4/2010 |
| JP | 2010-173739 | 8/2010 |
| JP | 2012-509740 | 4/2012 |
| JP | 2012-521221 | 9/2012 |
| JP | 2013-534451 | 9/2013 |
| JP | 2014-513583 | 6/2014 |
| MX | 6012309 | 1/2007 |
| WO | WO 88/003781 | 6/1988 |
| WO | WO 89/004150 | 5/1989 |
| WO | WO 93/010725 | 6/1993 |
| WO | WO 93/014721 | 8/1993 |
| WO | WO 94/000066 | 1/1994 |
| WO | WO 94/004088 | 3/1994 |
| WO | WO 95/035067 | 12/1995 |
| WO | WO 97/047246 | 12/1997 |
| WO | WO 98/048717 | 11/1998 |
| WO | WO 99/023963 | 5/1999 |
| WO | WO 00/024343 | 5/2000 |
| WO | WO 00/038582 | 7/2000 |
| WO | WO 00/053126 | 9/2000 |
| WO | WO 01/003570 | 1/2001 |
| WO | WO 01/030248 | 5/2001 |
| WO | WO 01/049191 | 7/2001 |
| WO | WO 01/078615 | 10/2001 |
| WO | WO 01/089428 | 11/2001 |
| WO | WO 02/045765 | 6/2002 |
| WO | WO 02/065954 | 8/2002 |
| WO | WO 02/096300 | 12/2002 |
| WO | WO 03/017856 | 3/2003 |
| WO | WO 03/071966 | 9/2003 |
| WO | WO 03/101350 | 12/2003 |
| WO | WO 2004/006792 | 1/2004 |
| WO | WO 2004/071358 | 8/2004 |
| WO | WO 2005/020850 | 3/2005 |
| WO | WO 2005/027760 | 3/2005 |
| WO | WO 2005/072661 | 8/2005 |
| WO | WO 2006/020464 | 2/2006 |
| WO | WO 2006/023980 | 3/2006 |
| WO | WO 2006/096803 | 9/2006 |
| WO | WO 2008/008522 | 1/2008 |
| WO | WO 2009/013397 | 1/2009 |
| WO | WO 2009/021876 | 2/2009 |
| WO | WO 2010/060072 | 5/2010 |
| WO | WO 2010/122472 | 10/2010 |
| WO | WO 2011/011621 | 1/2011 |
| WO | WO 2012/007941 | 1/2012 |
| WO | WO 2012/116266 | 8/2012 |
| WO | WO 2012/116267 | 8/2012 |
| WO | WO 2012/154265 | 11/2012 |
| WO | WO 2013/022880 | 2/2013 |
| WO | WO 2013/138655 | 9/2013 |
| WO | WO 2014/078541 | 5/2014 |

OTHER PUBLICATIONS

ArthroTek, "CurvTek® Bone Tunneling System," Surgical Technique, 2000, pp. 6.
E-mail from 3rd Party citing U.S. Appl. No. 60/721,909; U.S. Appl. No. 60/750,005 and U.S. Appl. No. 60/749,000, initial e-mail dated May 11, 2009, reply e-mail dated May 18, 2009.
King et al., "Mechanism of Spinal Injury Due to Caudocephalad Acceleration," Symposium on the Lumbar Spine, Orthopedic Clinic of North America, Jan. 1975, vol. 6, pp. 19-31.
PARTEQ Innovations, "Facet Joint Implants & Resurfacing Devices," Technology Opportunity Bulletin, Tech ID 1999-012, Queen's University, Ontario Canada.
Official Communication in Australian Application No. 2005213459, dated Dec. 11, 2009.
Official Communication in Australian Application No. 2005213459, dated Dec. 15, 2010.
Official Communication in Australian Application No. 2011226832, dated Sep. 4, 2012.
Official Communication in Australian Application No. 2011226832, dated Oct. 31, 2012.
Official Communication in Australian Application No. AU2013237744, dated Sep. 2, 2014.
Notice of Acceptance in Australian Application No. AU2013237744, dated Apr. 23, 2015.
Official Communication in Canadian Application No. 2,555,355, dated Sep. 2, 2011.

(56) References Cited

OTHER PUBLICATIONS

Official Communication in Canadian Application No. 2,803,783, dated Sep. 29, 2014.
Official Communication in Canadian Application No. 2,803,783, dated Aug. 5, 2015.
Official Communication in European Application No. 05712981.9, dated Jul. 24, 2007.
Official Communication in European Application No. 05712981.9, dated Mar. 10, 2008.
Official Communication in European Application No. 05712981.9, dated Apr. 6, 2009.
Official Communication in European Application No. 05712981.9, dated Jun. 15, 2010.
Official Communication in European Application No. 10178979.0, dated Mar. 14, 2011.
Official Communication in European Application No. 10178979.0, dated Nov. 13, 2012.
Official Communication in European Application No. 10178979.0, dated Aug. 5, 2013.
Official Communication in European Application No. 14175088.5, dated Sep. 8, 2014.
Official Communication in European Application No. 14175088.5, dated Nov. 18, 2015.
Official Communication in Japanese Application No. 2006-552309, dated May 25, 2010.
Official Communication in Japanese Application No. 2006-552309, dated Feb. 15, 2011.
Official Communication in Japanese Application No. 2010-221380, dated Feb. 15, 2011.
Official Communication in Japanese Application No. 2012-272106, dated Dec. 3, 2013.
Official Communication in Japanese Application No. 2012-272106, dated May 26, 2014.
Official Communication in Japanese Application No. 2012-272106, dated Feb. 23, 2015.
Official Communication in Japanese Application No. 2012-272106, dated Nov. 2, 2015.
International Search Report and Written Opinion in International Application No. PCT/US2005/003753, dated Dec. 5, 2006.
International Preliminary Report and Written Opinion in International App No. PCT/US2005/003753, dated Jan. 9, 2007.
Official Communication in Australian Application No. 2006227755, dated Dec. 8, 2010.
Official Communication in Australian Application No. 2012211502, dated Jul. 17, 2013.
Notice of Acceptance in Australian Application No. 2012211502, dated Sep. 10, 2014.
Official Communication in Australian Application No. 2014274519, dated Sep. 17, 2015.
Official Communication in European Application No. 06738204.4, dated Mar. 26, 2009.
Official Communication in European Application No. 06738204.4, dated Apr. 6, 2010.
Official Communication in European Application No. 06738204.4, dated Apr. 5, 2011.
Official Communication in European Application No. 06738204.4, dated Oct. 28, 2011.
Official Communication in European Application No. 06738204.4, dated Jul. 18, 2012.
Official Communication in European Application No. 06738204.4, dated Oct. 14, 2013.
Extended European Search Report for European Application No. 11160061.5, dated Nov. 2, 2011.
Official Communication in European Application No. 11160061.5, dated Sep. 9, 2012.
Extended European Search Report for European Application No. 11160063.1, dated Nov. 2, 2011.
Official Communication in European Application No. 11160063.1, dated Jul. 12, 2012.
Official Communication in European Application No. 11160063.1, dated Nov. 27, 2012.
Official Communication in European Application No. 11160063.1, dated Oct. 14, 2013.
Official Communication in European Application No. 14190344.3, dated Feb. 10, 2015.
Official Communication in European Application No. 14190344.3, dated Jan. 4, 2016.
Official Communication in Japanese Application No. 2008-501962, dated May 10, 2011.
Official Communication in Japanese Application No. 2008-501962, dated Nov. 13, 2012.
Official Communication in Japanese Application No. 2011-210533, dated Mar. 5, 2013.
Official Communication in Japanese Application No. 2011-210533, dated Dec. 3, 2013.
Notice of Allowance in Japanese Application No. 2011-210533, dated May 7, 2014.
Notice of Allowance in Japanese Application No. 2013-117602, dated May 7, 2014.
Notice of Allowance in Japanese Application No. 2013-117602, dated Feb. 2, 2015.
International Search Report and Written Opinion in International Application No. PCT/US2006/009120, dated Oct. 20, 2006.
International Preliminary Report and Written Opinion in International Application No. PCT/US2006/009120, dated Sep. 18, 2007.
Official Communication in European Application No. 08730413.5, dated Feb. 16, 2012.
Official Communication in European Application No. 14177951.2, dated Nov. 13, 2014.
International Search Report and Written Opinion in International Application No. PCT/US2008/054607, dated Jul. 10, 2008.
International Preliminary Report on Patentability in International Application No. PCT/US2008/054607, dated Sep. 3, 2009.
Official Communication in Australian Application No. 2011292297, dated Jul. 10, 2013.
Official Communication in European Application No. 11818586.7, dated Nov. 6, 2014.
Official Communication in Japanese Application No. 2013-524882, dated Mar. 2, 2015.
Official Communication in Japanese Application No. 2013-524882, dated Nov. 16, 2015.
International Search Report and Written Opinion in International Application No. PCT/US2011/047432, dated Dec. 12, 2011.
International Preliminary Report on Patentability in International Application No. PCT/US2011/047432, dated Feb. 28, 2013.
Official Communication in Australian Application No. AU2012222229, dated Aug. 21, 2015.
Official Communication in Australian Application No. AU2012222230, dated Aug. 21, 2015.
Official Communication in Japanese Application No. JP 2013-555591, dated Jan. 4, 2016.
Official Communication in Japanese Application No. JP 2013-555592, dated Dec. 7, 2015.
International Search Report in International Application No. PCT/US2012/026470, dated May 30, 2012.
International Preliminary Report on Patentability and Written Opinion in International Application No. PCT/US2012/026470, dated Sep. 6, 2013.
International Search Report and Written Opinion in International Application No. PCT/US2012/026472, dated Jun. 20, 2012.
International Preliminary Report on Patentability and Written Opinion in International Application No. PCT/US2012/026472, dated Mar. 12, 2014.
International Search Report and Written Opinion in International Application No. PCT/US2014/019302, dated May 18, 2015.
International Search Report and Written Opinion in International Application No. PCT/US2014/019325, dated Jun. 17, 2014.
International Preliminary Report on Patentability and Written Opinion in International Application No. PCT/US2014/019325, dated Sep. 24, 2015.
International Search Report and Written Opinion in International Application No. PCT/US2014/056598, dated Dec. 29, 2014.

(56) References Cited

OTHER PUBLICATIONS

International Search Report and Written Opinion in International Application No. PCT/US2015/050441, dated Dec. 28, 2015.
Official Communication in Japanese Application No. 2009-074336, dated Feb. 15, 2011.
International Search Report in International Application No. PCT/CA2002/000193 filed Feb. 15, 2002, dated Jun. 18, 2002.
International Search Report and Written Opinion in International Application No. PCT/US2004/028094, dated May 16, 2005.
International Preliminary Report on Patentability in International Application No. PCT/US2004/028094, dated Feb. 25, 2013.
International Search Report in International Application No. PCT/US2005/000987 filed Jan. 13, 2005, dated May 24, 2005.
International Preliminary Report on Patentability in International Application No. PCT/US2005/000987 filed Jan. 13, 2005, dated Jan. 17, 2006.
Official Communication in Australian Application No. 2014274519, dated Jun. 17, 2016.
Official Communication in Australian Application No. 2014274519, dated Aug. 26, 2016.
Notice of Acceptance in Australian Application No. 2014274519, dated Sep. 22, 2016.
Official Communication in European Application No. 14190344.3, dated Sep. 8, 2016.
International Search Report and Written Opinion in International Application No. PCT/US2016/013062, dated Mar. 16, 2016.
International Preliminary Report on Patentability and Written Opinion in International Application No. PCT/US2016/013062, dated Aug. 10, 2017.
Official Communication in Australian Application No. 2016277588, dated Sep. 7, 2017.
Ash, H.E., "Proximal Interphalangeal Joint Dimensions for the Design of a Surface Replacement Prosthesis", School of Engineering, University of Durham, Proceedings of the Institution of Mechanical Engineers Part H Journal of Engineering in Medicine Feb. 1996, vol. 210, No. 2, pp. 95-108.
Beaman, MD et al., "Substance P Innervation of Lumbar Spine Facet Joints", SPINE, 1993, vol. 18, No. 8, pp. 1044-1049.
Butterman, et al., "An Experimental Method for Measuring Force on the Spinal Facet Joint: Description and Application of the Method", Journal of Biomechanical Engineering, Nov. 1991, vol. 113, pp. 375-386.
Cruess et al., "The Response of Articular Cartilage to Weight-Bearing Against Metal", The Journal of Bone and Joint Surgery, Aug. 1984, vol. 66-B, No. 4, pp. 592-597.
Dalldorf et al., "Rate of Degeneration of Human Acetabular Cartilage after Hemiarthroplasty", The Journal of Bone and Joint Surgery, Jun. 1995, vol. 77. No. 6, pp. 877-882.
Frost, Harold M., "From Wolff's Law to the Utah Paradigm: Insights About Bone Physiology and Its Clinical Applications", The Anatomical Record, 2001, vol. 262, pp. 398-419.
Kurtz, PhD et al., "Isoelastic Polyaryletheretherketone Implants for Total Joint Replacement", PEEK Biomaterials Handbook, Ch. 14, 2012, pp. 221-226.
Meisel et al., "Minimally Invasive Facet Restoration Implant for Chronic Lumbar Zygapophysial Pain: 1-Year Outcomes", Annals of Surgical Innovation and Research (ASIR), 2014, vol. 8, No. 7, pp. 6.
Panjabi, PhD et al., "Articular Facets of the Human Spine: Quantitative Three-Dimensional Anatomy", SPINE, 1993, vol. 18, No. 10, pp. 1298-1310.
Ravikumar et al., "Internal Fixation Versus Hemiarthroplasty Versus Total Hip Arthroplasty for Displaced Subcapital Fractures of Femur—13 year Results of a Prospective Randomised Study", International Journal of the Care of the Injured (INJURY), 2000, vol. 31, pp. 793-797.
Schendel et al., "Experimental Measurement of Ligament Force, Facet Force, and Segment Motion in the Human Lumbar Spine", Journal of Biomechanics, 1993, vol. 26, No. 4/5, pp. 427-438.
Sharpe Products, "Metal Round Disks", https://web.archive.org/web/20170705214756/https://sharpeproducts.com/store/metal-round-disks, as archived Jul. 5, 2017 in 3 pages.
Tanno et al., "Which Portion in a Facet is Specifically Affected by Articular Cartilage Degeneration with Aging in the Human Lumbar Zygapophysial Joint?", Okajimas Folia Anatomica Japonica, May 2003, vol. 80, No. 1, pp. 29-34.
Official Communication in Australian Application No. AU2015205875, dated Apr. 2, 2016.
Official Communication in Australian Application No. AU2015205875, dated Jun. 15, 2016.
Official Communication in Australian Application No. AU2016231622, dated Dec. 5, 2017.
Official Communication in Canadian Application No. 2,803,783, dated Jul. 7, 2016.
Official Communication in Canadian Application No. 2,803,783, dated Apr. 5, 2017.
Official Communication in European Application No. 16180368.9, dated Mar. 31, 2017.
Official Communication in European Application No. 16180368.9, dated Jan. 11, 2018.
Official Communication in Australian Application No. 2014277721, dated Sep. 8, 2016.
Official Communication in Australian Application No. 2014277721, dated Jan. 9, 2017.
Official Communication in Canadian Application No. 2,804,223, dated Jun. 5, 2017.
Official Communication in Canadian Application No. 2,804,223, dated Mar. 14, 2018.
Official Communication in European Application No. 11818586.7, dated Feb. 3, 2017.
Official Communication in Japanese Application No. 2015-242990, dated Dec. 12, 2016.
Official Communication in Japanese Application No. 2015-242990, dated May 8, 2017.
Official Communication in Australian Application No. AU2012222229, dated May 11, 2016.
Official Communication in European Application No. EP12749447.4, dated Jan. 4, 2017.
Official Communication in European Application No. EP12749447.4, dated Apr. 4, 2017.
Official Communication in European Application No. 12749251.0, dated Jan. 4, 2017.
Official Communication in European Application No. 12749251.0, dated May 9, 2017.
Official Communication in Japanese Application No. 2016-246368, dated Oct. 30, 2017.
Official Communication in Japanese Application No. JP 2013-555592, dated Aug. 8, 2016.
Official Communication in Japanese Application No. Jp 2013-555592, dated Jan. 5, 2018.
Official Communication in Japanese Application No. 2016-237460, dated Oct. 23, 2017.
Official Communication in Australian Application No. 2014241989, dated Aug. 31, 2017.
Official Communication in European Application No. 14774714.1, dated Oct. 21, 2016.
Official Communication in Japanese Application No. JP 2016-500490, dated Nov. 27, 2017.
Official Communication in Australian Application No. 2014241994, dated Oct. 30, 2017.
Official Communication in European Application No. 14776445.0, dated Nov. 7, 2016.
Official Communication in Japanese Application No. JP 2016-500498, dated Jan. 5, 2018.
Official Communication in European Application No. 14850082.0, dated Aug. 31, 2016.
International Preliminary Report on Patentability and Written Opinion in International Application No. PCT/US2014/056598, dated Apr. 7, 2016.
International Preliminary Report on Patentability and Written Opinion in International Application No. PCT/US2015/050441, dated Mar. 30, 2017.

(56) References Cited

OTHER PUBLICATIONS

ArthroTek, "CurvTek® Bone Tunneling System," User's Manual, 2000, pp. 20.
Official Communication in Japanese Application No. 2015-242990, dated Aug. 21, 2017.
Official Communication in Japanese Application No. JP 2013-555591, dated Nov. 21, 2016.
Official Communication in Australian Application No. AU2016231622, dated Nov. 22, 2018.
Official Communication in European Application No. 18150661.9, dated May 25, 2018.
Official Communication in European Application No. EP12749447.4, dated Nov. 14, 2018.
Official Communication in Japanese Application No. 2016-246368, dated Jul. 2, 2018.
Official Communication in Japanese Application No. 2016-237460, dated Apr. 16, 2018.
Official Communication in Australian Application No. 2014241989, dated Jun. 20, 2018.
Official Communication in Australian Application No. 2014241989, dated Aug. 17, 2018.
Official Communication in Japanese Application No. JP 2016-500490, dated May 7, 2018.
Official Communication in Japanese Application No. JP 2016-500498, dated Jul. 2, 2018.
Official Communication in Australian Application No. 2014327083, dated May 31, 2018.
Official Communication in Japanese Application No. JP 2016-517392, dated Jun. 4, 2018.
Official Communication in European Application No. 16743832.4, dated Jul. 24, 2018.
Notice of Acceptance in Australian Application No. AU2016231622, dated Dec. 4, 2018.
Official Communication in Australian Application No. AU2019201539, dated Jun. 25, 2019.
Official Communication in European Application No. 19158915.9, dated Jul. 1, 2019.
Official Communication in European Application No. 14774714.1, dated May 23, 2019.
Official Communication in Japanese Application No. JP 2016-500498, dated Mar. 4, 2019.
Notice of Acceptance in Australian Application No. 2014327083, dated Apr. 3, 2019.
Official Communication in Japanese Application No. JP 2016-517392, dated Apr. 22, 2019.
Official Communication in European Application No. 12749251.0, dated Aug. 16, 2019.
Official Communication in Japanese Application No. JP 2016-500498, dated Aug. 9, 2019.
Official Communication in Japanese Application No. JP 2016-517392, dated Dec. 2, 2019.
Official Communication in Australian Application No. 2016212009, dated Sep. 6, 2019.
Official Communication in Japanese Application No. 2017-557269, dated Oct. 21, 2019.
International Search Report and Written Opinion in International Application No. PCT/US2019/052211, dated Feb. 3, 2020.
Invitation to Pay Additional Search Fees in International Application No. PCT/US2019/052211, dated Nov. 14, 2019.

* cited by examiner

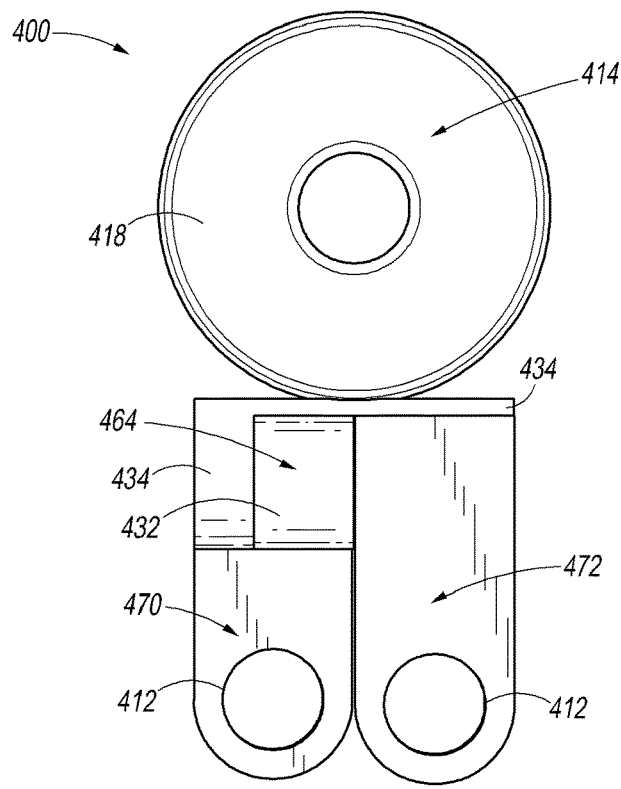
FIG. IIA
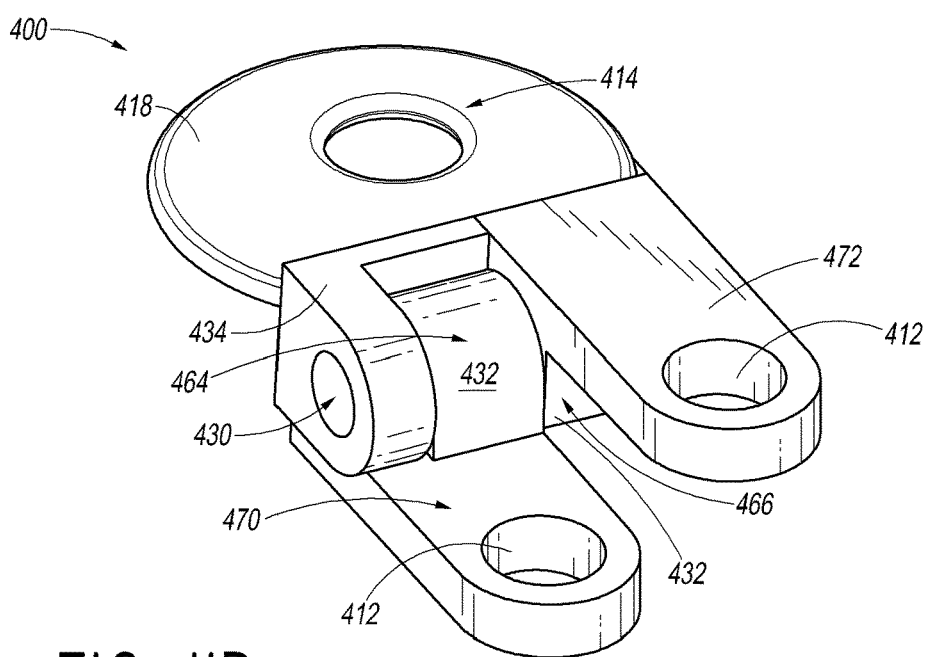
FIG. IIB

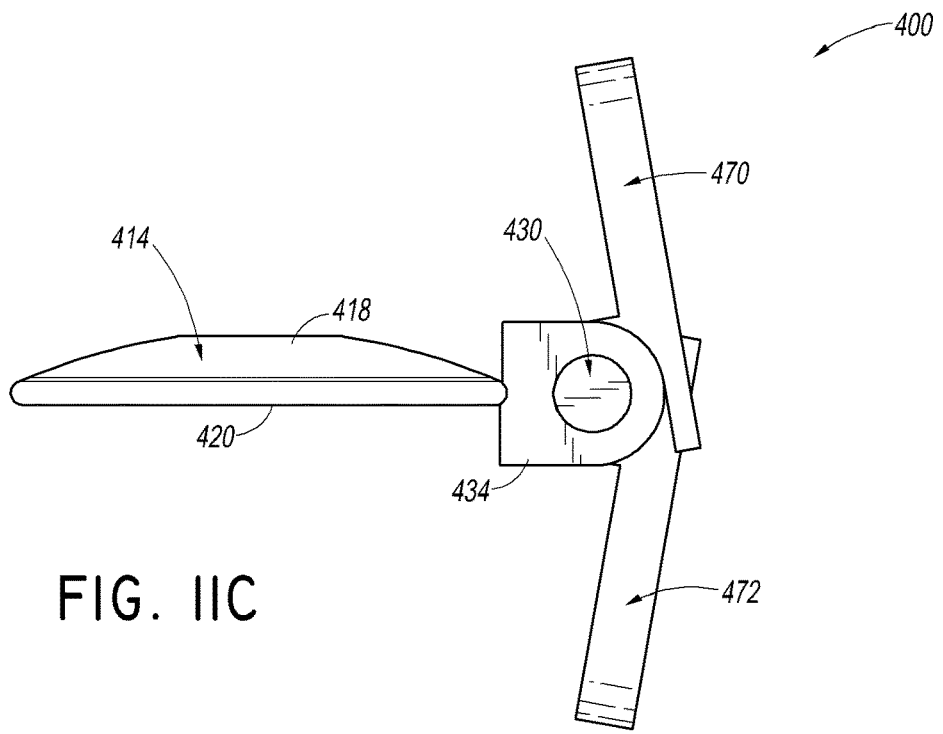
FIG. IIC
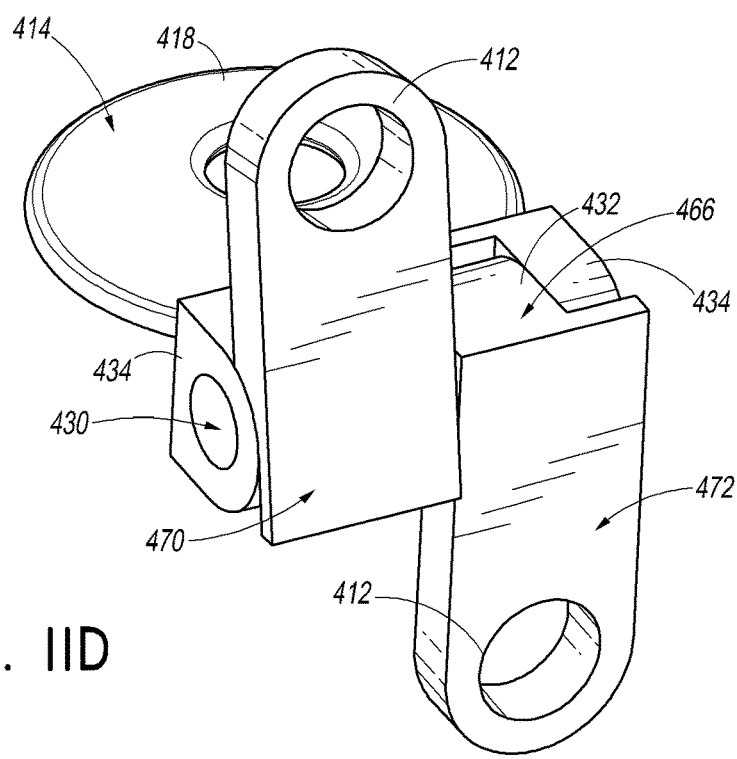
FIG. IID

FACET JOINT IMPLANT

INCORPORATION BY REFERENCE TO ANY PRIORITY APPLICATIONS

This application claims priority benefit to U.S. Provisional Patent Application No. 62/108,451, filed Jan. 27, 2015, the entirety of which is hereby incorporated by reference herein.

BACKGROUND

Field

Some embodiments described herein relate generally to methods and apparatus for stabilizing bone, for example, stabilizing vertebrae by securing the articular processes of the vertebrae.

Description of the Related Art

Traumatic, inflammatory, and degenerative disorders of the spine can lead to severe pain and loss of mobility. One source of back and spine pain is related to degeneration of the facets of the spine or facet arthritis. Bony contact or grinding of degenerated facet joint surfaces can play a role in some pain syndromes. While many technological advances have focused on the intervertebral disc and artificial replacement or repair of the intervertebral disc, little advancement in facet repair has been made. Facet joint and disc degeneration frequently occur together. Thus, a need exists to address the clinical concerns raised by degenerative facet joints.

The current standard of care to address the degenerative problems with the facet joints is to fuse the two adjacent vertebrae. By performing this surgical procedure, the relative motion between the two adjacent vertebrae is stopped, thus stopping motion of the facets and any potential pain generated as a result thereof. Procedures to fuse two adjacent vertebrae often involve fixation and/or stabilization of the two adjacent vertebrae until the two adjacent vertebrae fuse.

Injuries and/or surgical procedure on and/or effecting other bones can also result in the desire to fixate and/or stabilize a bone until the bone, or bone portions, can fuse, for example, to stabilize a sternum after heart surgery, to stabilize a rib after a break, etc. Current procedures to fixate and/or stabilize adjacent vertebrae and/or other bones can be slow and/or complex.

Accordingly, a need exists for an apparatus and a procedure to quickly and/or easily stabilize and/or fixate vertebrae.

SUMMARY

Devices and methods are disclosed for treating the facet joint. An implant for treating the facet joint is provided. In some embodiments, the implant comprises a fixation plate having an access surface and a bone facing surface, a spacer configured to be placed in the facet joint, and at least one hinge between the spacer and the bone facing surface of the fixation plate.

In some embodiments, the spacer is a disc. In some embodiments, the fixation plate has a plurality of holes. In some embodiments, the spacer has a plurality of holes. In some embodiments, at least one of the plurality of holes in the spacer comprises graft materials. In some embodiments, the at least one hinge provides for pivoting articulation and movement between the spacer and the fixation plate. In some embodiments, the fixation plate comprises an upper portion comprising at least one hole configured to accept a bone screw there through. In some embodiments, the fixation plate comprises a lower portion comprising at least one hole configured to accept a bone screw there through. In some embodiments, the at least one hinge comprises a pair of hinges. In some embodiments, the implant comprises a low profile configuration wherein the fixation plate is substantially parallel to an inferior surface of the spacer. In some embodiments, the fixation plate is configured to rotate to a second configuration wherein the fixation plate is substantially perpendicular to a superior surface of the spacer.

A method for treating a facet joint comprising a superior articular process and an inferior articular process is provided. The method can comprise the step of implanting a spacer between the superior articular process and the inferior articular process. The method can comprise the step of positioning a fixation plate over the facet joint. The method can comprise the step of securing the fixation plate to at least one of the superior articular process and the inferior articular process.

In some embodiments, positioning the fixation plate further comprises pivoting the fixation plate relative to the spacer about a hinge. In some embodiments, securing the fixation plate further comprises inserting a screw through a hole in the fixation plate. In some embodiments, the method can comprise the step of inserting graft material into a hole in the spacer. In some embodiments, the method can comprise the step of rotating the fixation plate to a low profile configuration wherein the fixation plate is substantially parallel to an inferior surface of the spacer. In some embodiments, wherein the step of positioning the fixation plate over the facet joint further comprises rotating the fixation plate to a position substantially perpendicular to a superior surface of the spacer.

A method for treating a spine is provided. The method can comprise the step of providing an implant comprising a fixation plate having an access surface and a bone facing surface, a spacer, and at least one hinge between the spacer and the bone facing surface of the fixation plate. The method can comprise the step of inserting the spacer into a facet joint between a first vertebra and a second vertebra. The method can comprise the step of attaching the fixation plate to the first vertebra. In some embodiments, the method can comprise the step of attaching the fixation plate to the second vertebra. In some embodiments, the method can comprise the step of attaching a second fixation plate to the second vertebra.

The above embodiments and methods of use are explained in more detail below.

BRIEF DESCRIPTION OF THE DRAWINGS

The structure and method of use will be better understood with the following detailed description of embodiments, along with the accompanying illustrations, in which:

FIGS. 11A to 11D are various views of an embodiment of an implant comprising a pair of pivoting fixation plates and spacer.

DETAILED DESCRIPTION

A. Anatomy of the Spine

Figure 1:
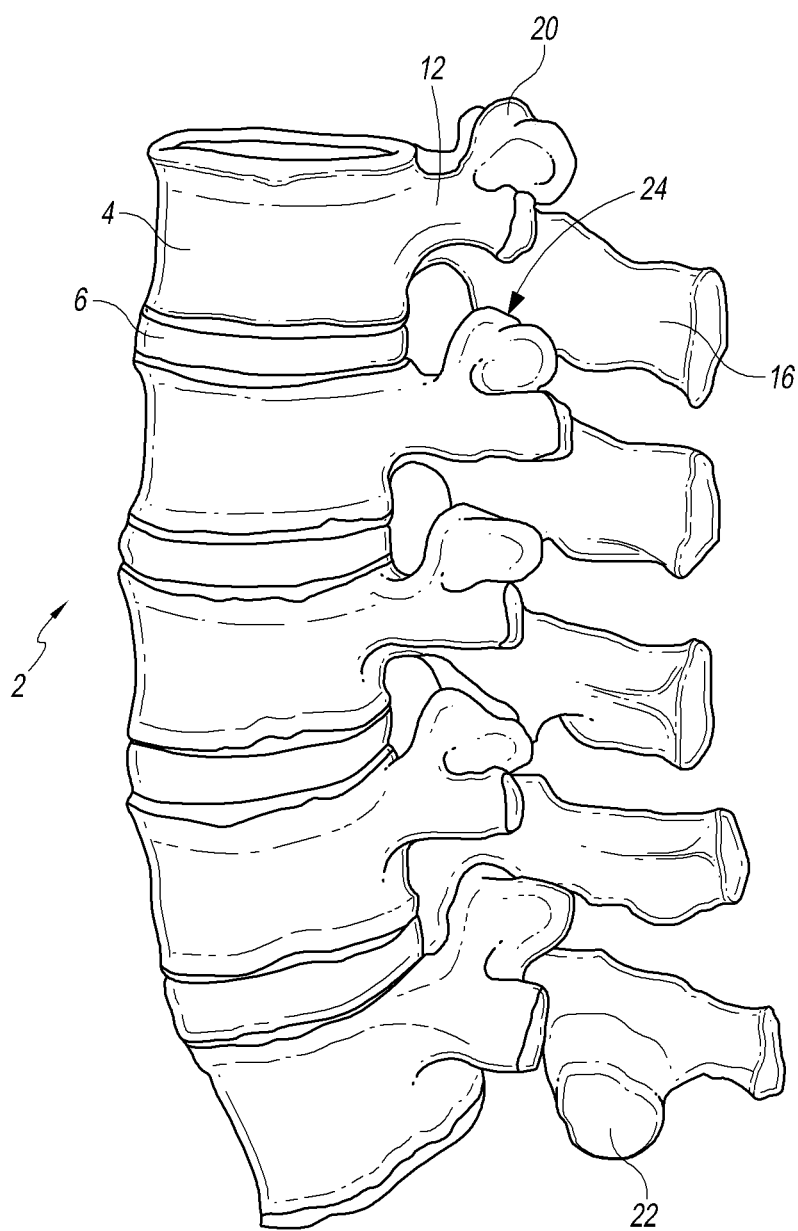
FIG. 1 is a lateral elevational view of a portion of the vertebral column.
Figure 2A:
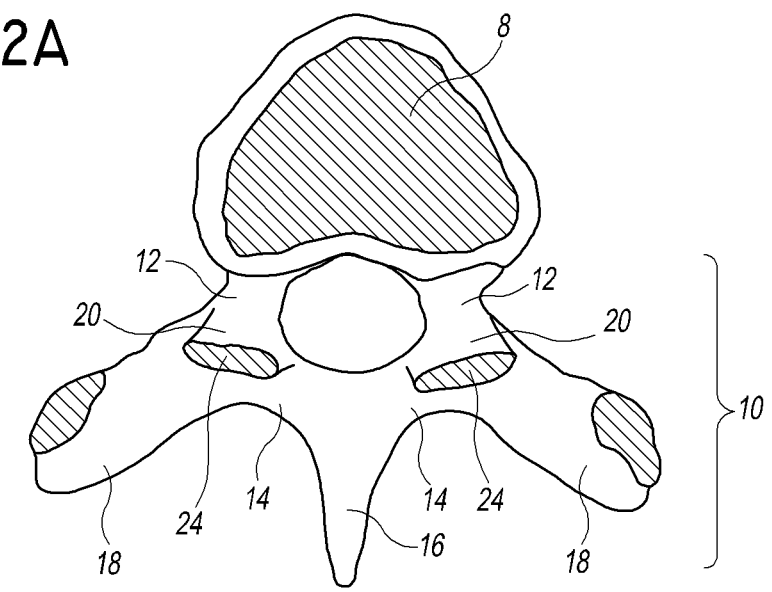
FIG. 2A is a schematic superior view of an isolated thoracic vertebra.
Figure 2B:
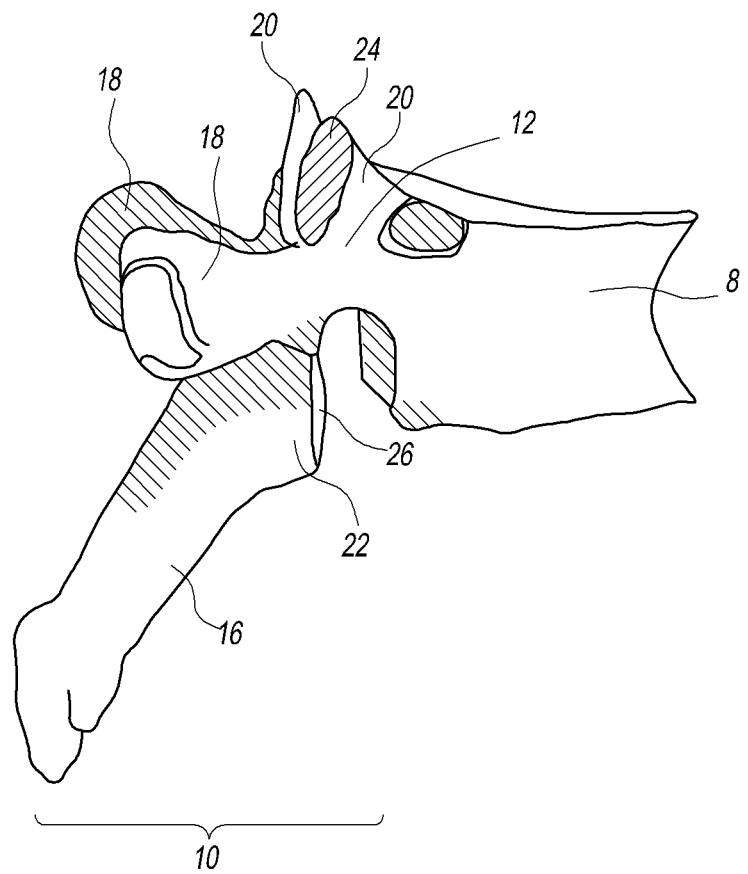
FIG. 2B is a schematic side view of an isolated thoracic vertebra.
Figure 3A:
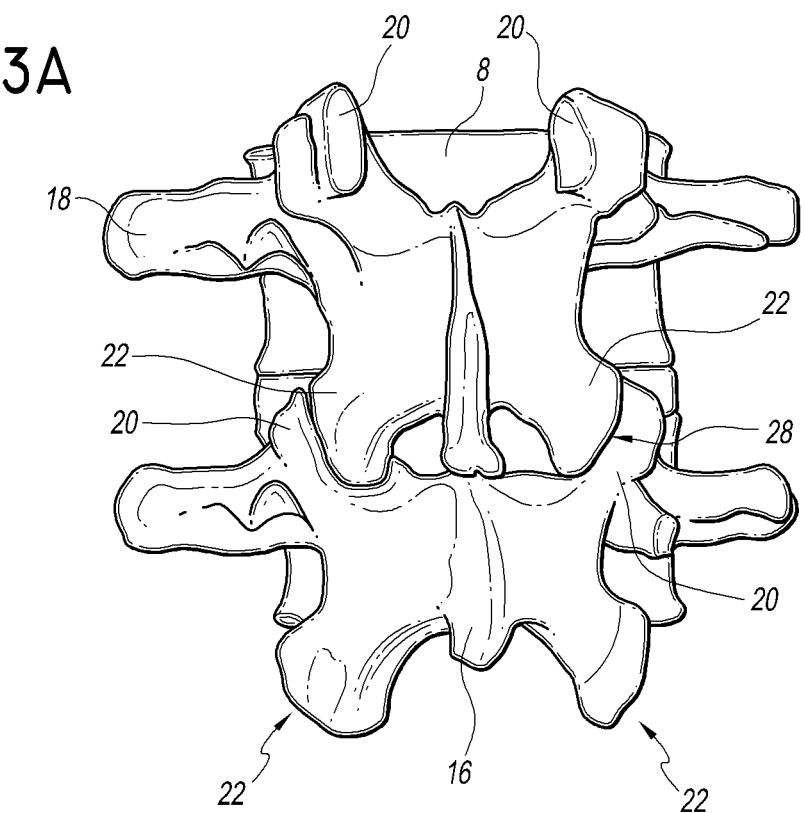
FIG. 3A is a schematic posterior elevational view of a portion of the vertebral column.
Figure 3B:
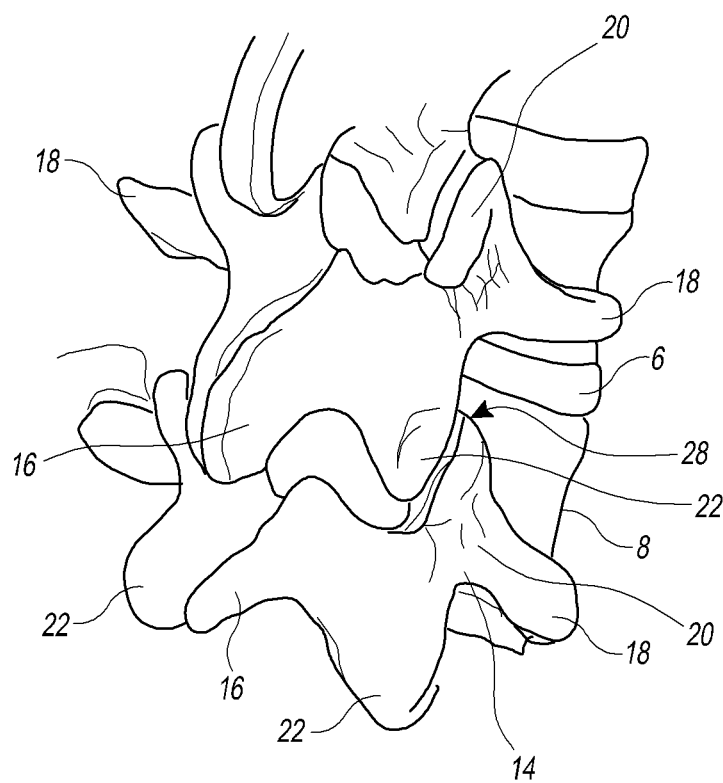
FIG. 3B is a posterior-oblique elevational view of a portion of the vertebral column.
Figure 4A:
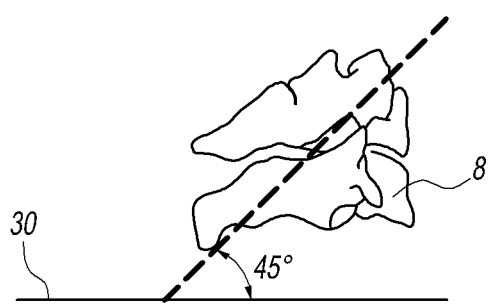
FIG. 4A is a schematic side view of a facet joint in the cervical vertebrae.
Figure 4B:
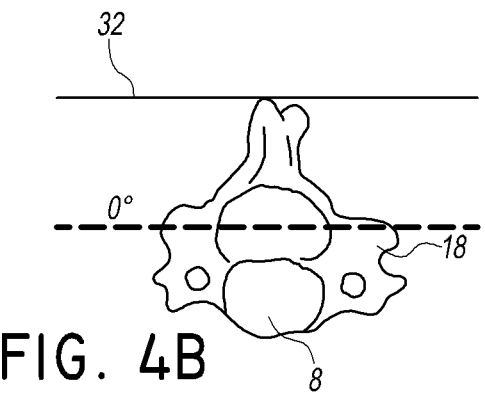
FIG. 4B is a schematic superior view of a facet joint in the cervical vertebrae.

As shown in FIG. 1, the vertebral column 2 comprises a series of alternating vertebrae 4 and fibrous discs 6 that provide axial support and movement to the upper portions of the body. The vertebral column 2 typically comprises thirty-three vertebrae 4, with seven cervical (C1-C7), twelve thoracic (T1-T12), five lumbar (L1-15), five fused sacral (S1-S5) and four fused coccygeal vertebrae. FIGS. 2A and 2B depict a typical thoracic vertebra. Each vertebra includes an anterior body 8 with a posterior arch 10. The posterior arch 10 comprises two pedicles 12 and two laminae 14 that join posteriorly to form a spinous process 16. Projecting from each side of the posterior arch 10 is a transverse 18, superior articular process 20 and inferior articular process 22. The facets 24, 26 of the superior 20 and inferior articular processes 22 form facet joints 28 with the articular processes of the adjacent vertebrae (see FIGS. 3A and 3B). The facet joints are true synovial joints with cartilaginous surfaces and a joint capsule.

Figure 5A:
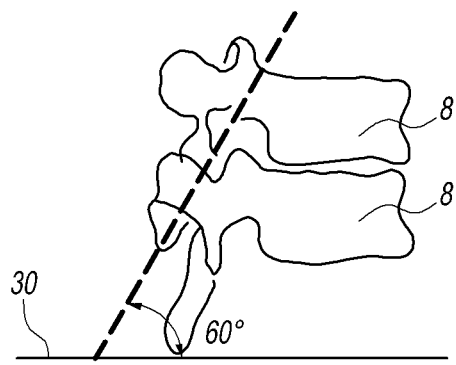
FIG. 5A is a schematic side view of a facet joint in the thoracic vertebrae.
Figure 5B:
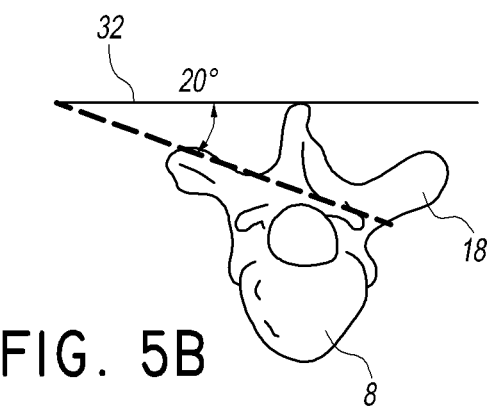
FIG. 5B is a schematic superior view of a facet joint in the thoracic vertebrae.
Figure 6A:
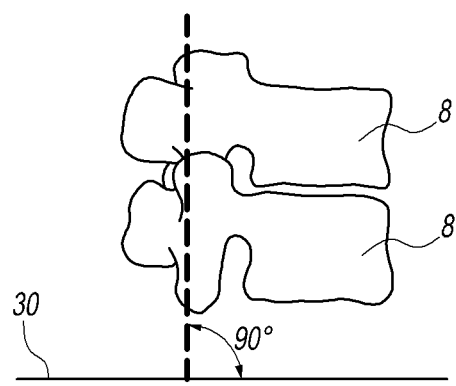
FIG. 6A is a schematic side view of a facet joint in the lumbar vertebrae.
Figure 6B:
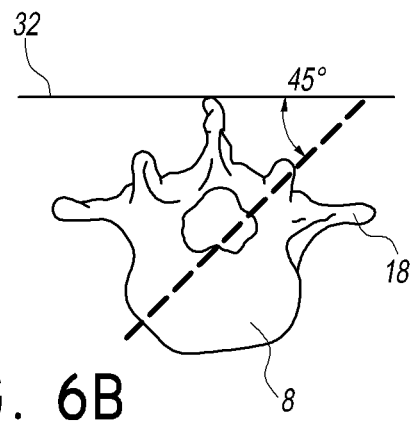
FIG. 6B is a schematic superior view of a facet joint in the lumbar vertebrae.

The orientation of the facet joints vary, depending on the level of the vertebral column. In the C1 and C2 vertebrae, for example the facet joints are parallel to the transverse plane. FIGS. 4A to 6B depict examples of the orientations of the facet joints at different levels of the vertebral column. In the C3 to C7 vertebrae examples shown in FIGS. 4A and 4B, the facets are oriented at a 45-degree angle to the transverse plane 30 and parallel to the frontal plane 32, respectively. This orientation allows the facet joints of the cervical vertebrae to flex, extend, lateral flex and rotate. At a 45-degree angle in the transverse plane 30, the facet joints of the cervical spine can guide, but do not limit, the movement of the cervical vertebrae. FIGS. 5A and 5B depict examples of the thoracic vertebrae, where the facets are oriented at a 60-degree angle to the transverse plane 30 and a 20-degree angle to the frontal plane 32, respectively. This orientation is capable of providing lateral flexion and rotation, but only limited flexion and extension. FIGS. 6A and 6B illustrate examples of the lumbar region, where the facet joints are oriented at 90-degree angles to the transverse plane 30 and a 45-degree angle to the frontal plane 32, respectively. The lumbar vertebrae are capable of flexion, extension and lateral flexion, but little, if any, rotation because of the 90-degree orientation of the facet joints in the transverse plane. The actual range of motion along the vertebral column can vary considerably with each individual vertebra.

In addition to guiding movement of the vertebrae, the facet joints also contribute to the load-bearing ability of the vertebral column. One study by King et al. Mechanism of Spinal Injury Due to Caudocephalad Acceleration, Orthop. Clin. North Am., 6:19 1975, found facet joint load-bearing as high as 30% in some positions of the vertebral column. The facet joints may also play a role in resisting shear stresses between the vertebrae. Over time, these forces acting on the facet joints can cause degeneration and arthritis.

B. Facet Joint Implant

Figure 7:
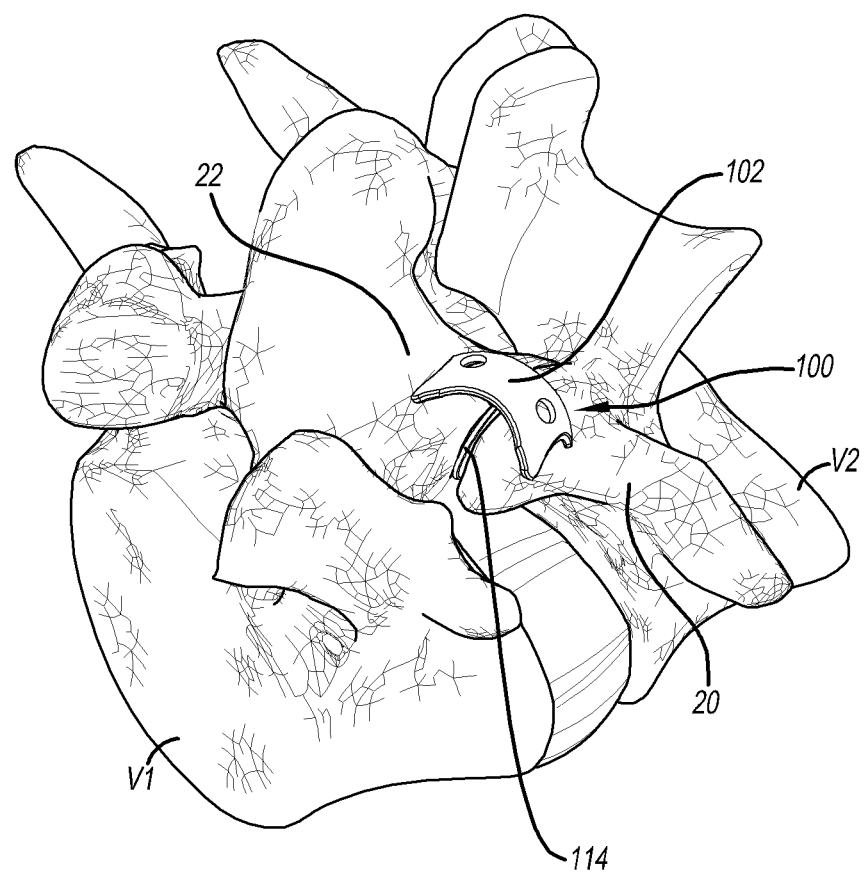
FIG. 7 is a view of an embodiment of an implant inserted into a facet joint.

FIG. 7 shows an embodiment of a facet joint implant 100. As shown in FIG. 7, the implant 100 can comprise a fixation plate 102 and a spacer 114. The spacer 114 can be placed between the facets of the superior and inferior articular processes 20, 22. The orientation of the spacer 114 can depend on the facet joint. The spacer 114 can be placed in the facet joint located at any level of the vertebral column. For instance, the spacer 114 can be parallel to the transverse plane if the spacer 114 is located in a facet joint between the C1 and C2 vertebrae. The spacer 114 can be placed at any angle to the transverse plane, including parallel, substantially parallel, perpendicular, substantially perpendicular, 0 degrees, 15 degrees, 30 degrees, 45-degrees, 60 degrees, 75 degrees, 90 degrees, etc. The spacer 114 can be placed at any angle to the frontal plane, including parallel, substantially parallel, perpendicular, substantially perpendicular, 0 degrees, 15 degrees, 30 degrees, 45-degrees, 60 degrees, 75 degrees, 90 degrees, etc. In some embodiments, the fixation plate 102 covers a portion of the facet joint 28. The fixation plate 102 can be secured to the superior articular process 20, the inferior articular process 22, or both the superior and inferior articular processes 20, 22. The fixation plate 102 can prevent migration of the spacer 114 from the facet joint 28. The fixation plate 102 can facilitate fusion of the articular processes 20, 22. In some embodiments, the fixation plate 102 is joined or coupled to the spacer 114. In other embodiments, the fixation plate 102 and the spacer 114 are separate components.

1. Spacer

Figure 8A:
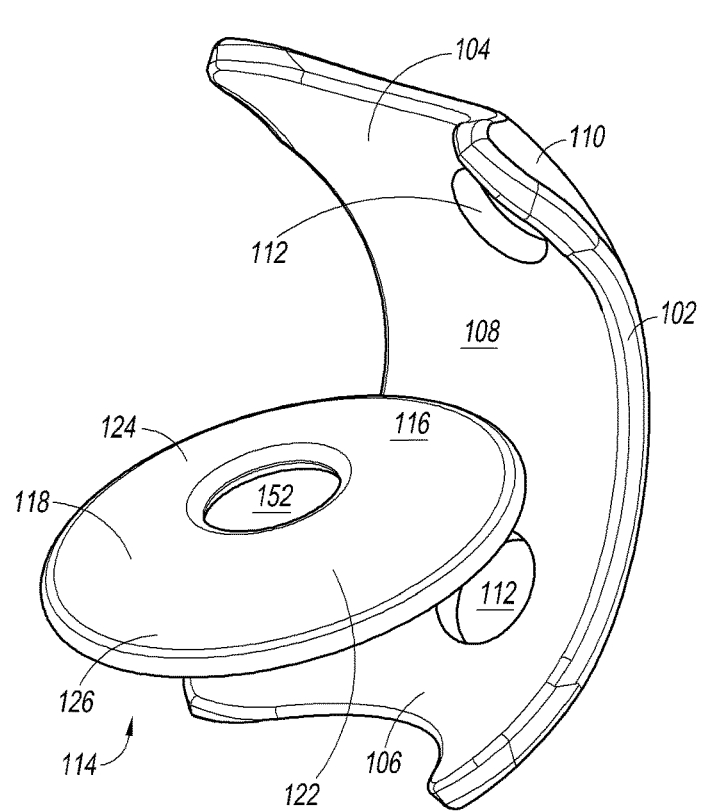
FIGS. 8A to 8B are various views of an embodiment of an implant comprising a separate fixation plate and spacer.
Figure 8B:
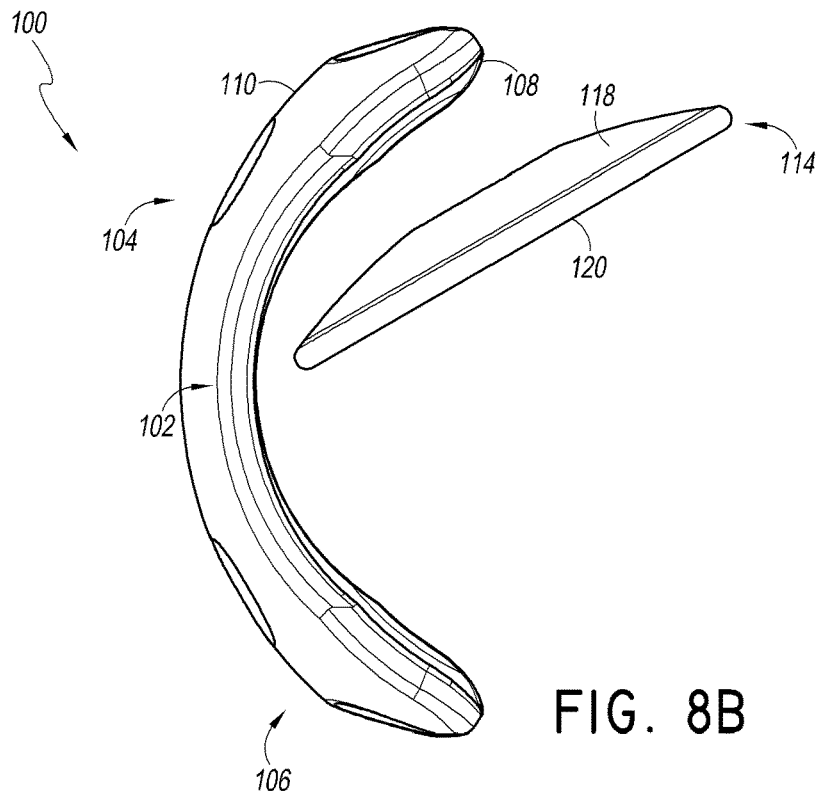
Figure 9A:
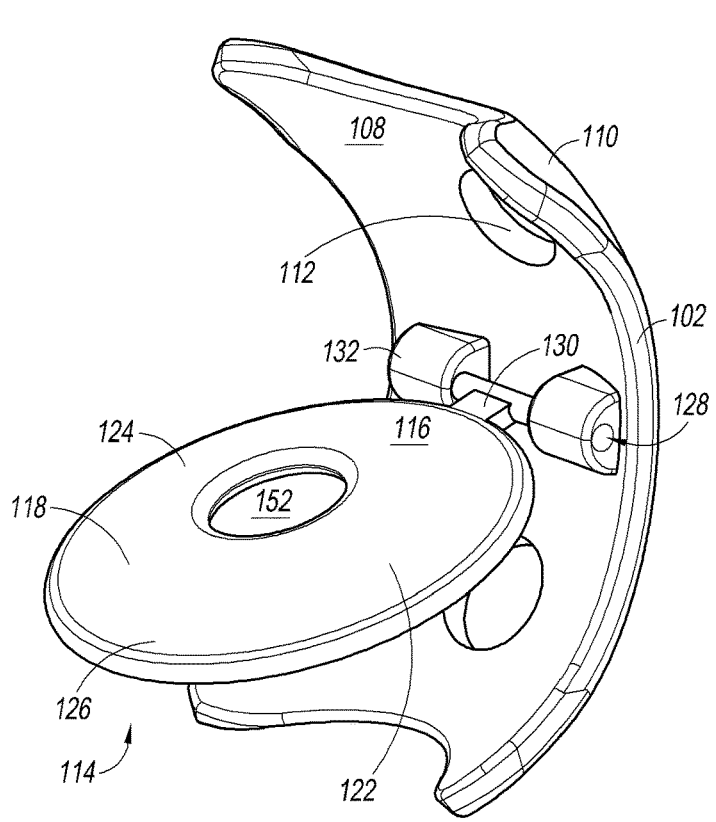
FIGS. 9A to 9D are various views of an embodiment of an implant comprising a pivoting fixation plate and spacer.
Figure 9B:
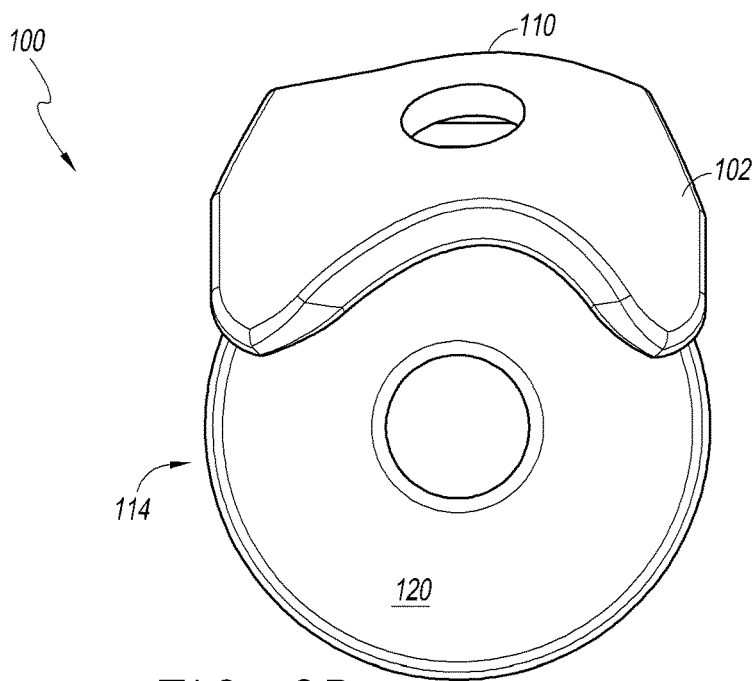
Figure 9C:
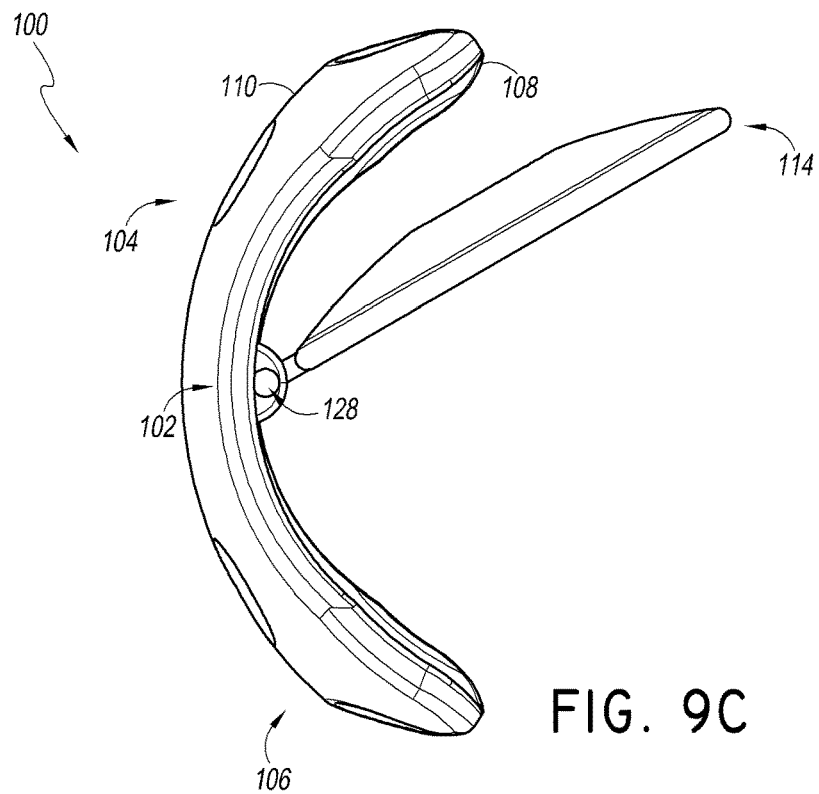
Figure 9D:
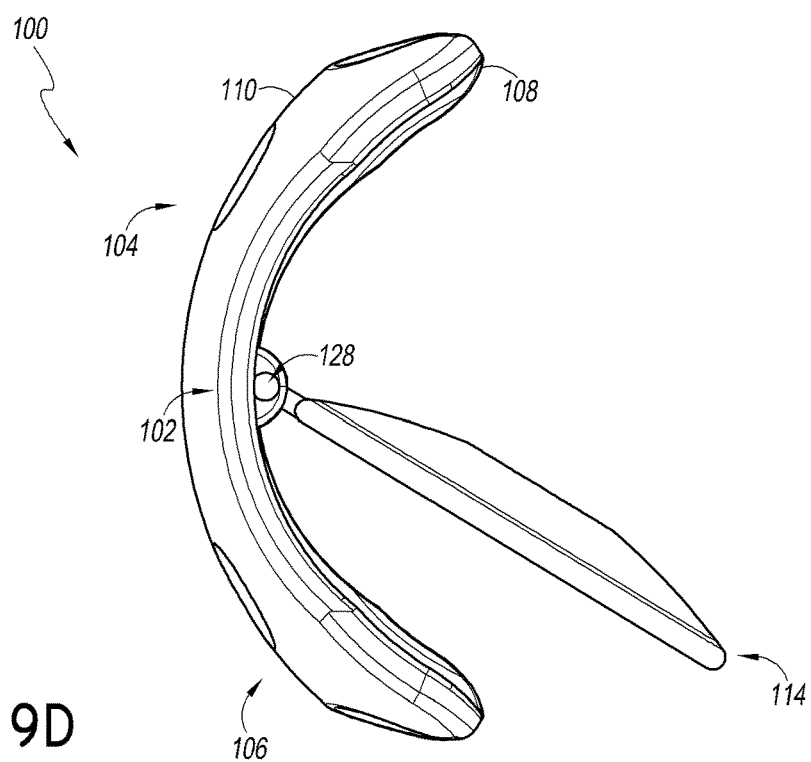

In some embodiments, a spacer 114 for restoring or maintaining the spacing between two facets 24, 26 of a facet joint 28 is provided. As shown in FIGS. 8A through 8B, the implant 100 can comprise the spacer 114 with a least two faces, a superior surface 118 adapted to contact the articular surface of one facet of the facet joint 28 and an inferior surface 120 adapted to contact the articular surface of the other facet of the facet joint 28. For instance, in some embodiments, the superior surface 118 is shaped to contact the superior articular process 20 and the inferior surface 120 is shaped to contact the inferior articular process 22.

As shown in FIGS. 8A through 8B, the spacer 114 can be substantially disc shaped. In some embodiments, the spacer 114 has a generally circular profile and is sized to fit generally within the joint capsule of the facet joint 28. In other embodiments, the spacer 114 can be other shapes, e.g., square, elliptical, or any other shape. The spacer 114 can have any of a variety of three dimensional shapes, including but not limited to a rectangular box, a trapezoidal box, H-shaped, O-shaped, V-shaped, with or without one or more lumens within the spacer 114. In other embodiments, the spacer 114 can have any of a variety of profiles, including but not limited to square, rectangle, oval, star, octagonal, polygon or combination thereof. In some embodiments, the spacer 114 having the desired shape is selected from an array of spacers after radiographic visualization of the articular processes and/or by radio-contract injection into the facet joint to visualize the joint capsule.

In some embodiments, the spacer 114 has a diameter of about 4 mm to about 30 mm. In another embodiment, the spacer 114 has a diameter of about 5 mm to about 25 mm. In still another embodiment, the spacer 114 has a diameter of about 10 mm to about 20 mm. In some embodiments, the spacer 114 has a cross-sectional area of about 10 $mm^2$ to about 700 $mm^2$. In another embodiment, the spacer 114 has a cross-sectional area of about 25 $mm^2$ to about 500 $mm^2$. In still another embodiment, the spacer 114 has a cross-sectional area of about 20 $mm^2$ to about 400 $mm^2$, and preferably about 25 $mm^2$ to about 100 $mm^2$.

The spacer 114 has a thickness generally equal to about the anatomic spacing between two facets 24, 26 of a facet joint 28. The spacer 114 generally has a thickness within the range of about 0.5 mm to about 3.0 mm. In certain embodiments, the spacer 114 has a thickness of about 1 mm to about 2 mm. In some embodiments, the spacer 114 has a thickness of about 0.5 mm to about 1.5 mm. In some embodiments, the thickness of the spacer 114 is non-uniform within the same spacer. For example, the thickness of the spacer 114 can be increased around the entire outer edge, along at least one and, both superior and inferior surfaces 118, 120. In some embodiments, only a portion of the outer edge of the spacer 114 has a thickness that is greater than the thickness of a central region, and, optionally, also thicker than the typical anatomic spacing between two facets 24, 26 of a facet joint 28. An increased edge thickness may resist lateral displacement of the spacer 114 out of the facet joint 28.

In some embodiments, the spacer 114 is configured to provide an improved fit with one or more of the articular processes 20, 22 and/or joint capsule of the facet joint 28. For example, in some embodiments, the spacer 114 has a bend, angle or curve to generally match the natural shape of an articular facet. The spacer 114 may be rigid with a preformed bend. Alternatively, the spacer 114 may be sufficiently malleable that it will conform post implantation to the unique configuration of the adjacent facet face. In some embodiments, the spacer 114 is configured to be implanted between the articular processes 20, 22 and/or within the joint capsule of the facet joint 28, without securing of the spacer 114 to any bony structures. Such embodiments can thus be used without invasion or disruption of the articular process and/or structure, thereby maintaining the integrity of the articular process and/or structure.

In some embodiments, at least a portion of one surface of the spacer 114 is highly polished. For instance, the superior surface 118 and/or the inferior surface 120 can be highly polished. A highly polished portion of the spacer 114 may reduce the surface friction and/or wear in that portion of the spacer 114 as it contacts bone, cartilage or another surface of the spacer 114. A highly polished surface on the spacer 114 may also decrease the risk of the spacer 114 wedging between the articular surfaces of the facet joint 28, which can cause pain and locking of the facet joint 28.

In some embodiments, at least a portion of one surface of the spacer 114 has a roughened surface. For instance, the superior surface 118 and/or the inferior surface 120 can be roughened. A roughened surface may be advantageous when in contact with a bone or tissue surface because it may prevent slippage of the spacer 114 against the bone and aid in maintaining the spacer 114 in the facet joint 28. In some embodiments, at least a portion of one surface of the spacer 114 has a porous surface. For instance, the superior surface 118 and/or the inferior surface 120 can be porous. A porous surface can be created in any a variety of ways known in the art, such as by applying sintered beads, spraying plasma onto the surfaces of the spacer 114, or spraying a titanium coating onto the surfaces of the spacer 114. A porous surface can allow bone to grow into or attach to the surface of the spacer 114, thus securing the spacer 114 to the bone. In some embodiments, an adhesive or sealant, such as a cyanoacrylate, polymethylmethacrylate, or other adhesive known in the art, is used to bond one surface of the spacer 114 to an articular surface. Bone growth facilitators, electrical current, or other known techniques may be used to accelerate osteoincorporation of textured or microporous anchoring surfaces of the spacer 114.

In some embodiments, a first surface of spacer 114 is roughened or porous and a second surface is highly polished. For instance, the roughened first surface can be the superior surface 118 and highly polished second surface can be the inferior surface 120. The first surface contacts or engages one facet of the facet joint 28 and aids in maintaining the spacer 114 between the articular surfaces. The second surface contacts or engages the other facet of the facet joint 28 to provide or allow for movement at that facet joint 28. In some embodiments, the spacer 114 comprises a curved or bent disc with a roughened surface on the greater face of the disc and a highly polished surface on the lesser face. The spacer 114 generally maintains a fixed position relative to the facet contacting the roughened surface while the movement of the facet joint 28 is preserved between the other facet and the highly polished lesser face of the spacer 114.

In some embodiments (not shown), the spacer comprises two separate discs, each disc comprising a first face that articulates with the complementary first face of the other disc, and a second face adapted to secure the disc to the adjacent bone or cartilage of one facet of the facet joint 28. In some embodiments, the thickness of one disc will generally be about half of the anatomic spacing between two facets 24, 26 of the facet joint 28. In other embodiments, the spacer comprises three or more discs. In some embodiments, the total thickness of all the discs is generally about 25% to about 300% of the anatomic spacing between the two facets 24, 26. In another embodiment, the total thickness of the discs is generally about 50% to about 150% of the anatomic spacing. In still another embodiment, the total thickness of the discs is about 75% to about 125% of the anatomic spacing. Each disc of the two-part spacer can otherwise also have features similar to those of a single-disc spacer 114, including but not limited to curved or bent configurations, highly polished or roughened surfaces, and other feature mentioned herein. The two or more discs need not have the same size, thickness, configuration or features.

In some embodiments, the spacer 114 is maintained between the two facets 24, 26 of the facet joint 28 by taking advantage of the joint capsule and/or other body tissue surrounding the facet joint 28 to limit the migration of the spacer 114 out of the facet joint 28. In some embodiments, the shape of the spacer 114 is capable of resisting displacement of the spacer 114 from its position generally between the facet joint surfaces. In some embodiments, a concave or biconcave configuration resists displacement of the spacer 114 by providing an increased thickness at the periphery of the spacer 114 that requires a larger force and/or greater distraction of facet joint surfaces in order to cause displacement. In other embodiments, surface treatments or texturing are used to maintain the spacer 114 against a facet of the facet joint 28, as described herein. In some embodiments, a combination of disc configuration, surface texturing and existing body tissue or structures are used to maintain the position of the spacer 114. In some embodiments, an adhesive is used to maintain the position of the spacer 114. In some embodiments, the fixation plate 102 is used to maintain the position of the spacer 114 within the facet joint 28.

The spacer 114 can comprise any structure configured to maintain a separation and resist compression between two articular processes 20, 22 which form a facet joint 28. The spacer 114 can be implanted and deployed to restore the space between facets of the superior articular process 20 of a vertebra and the inferior articular process 22 of an adjacent vertebra. The spacer 114 can be implanted and deployed to help stabilize or fuse adjacent vertebrae. The spacer 114 can be implanted and deployed to deliver a medication.

As shown in FIGS. 8A through 8B, the spacer 114 can have a superior surface 118 and an inferior surface 120, a posterior side 116 and an anterior side 126, and lateral sides 122, 124. Each surface 118, 120 need not be flat, and can be curved or undulating or any combination thereof. As shown in FIG. 8A, the superior surface 118 is convex and the inferior surface 120 is concave. In some embodiments, the superior surface 118 and/or the inferior surface 120 can be convex, concave, or flat. In other words, the superior surface 118 can be concave, convex, or flat, and the inferior surface 120 can be concave, convex, or flat, e.g., the superior surface 118 is concave and the inferior surface 120 is concave, the superior surface 118 concave and the inferior surface 120 is convex, etc. In this manner, the superior surface 118 and the inferior surface 120 can fit better against the articular processes 20, 22, specifically against the facets 24, 26 of the articular processes 20, 22 of adjacent vertebrae forming the facet joint 28. In some embodiments, the spacer 114 can include substances configured to release medication and/or increase the stability of the facet joint 28. As discussed herein, the substances can include a medicine(s) and/or an adhesive(s).

The superior and inferior surfaces 118, 120 can be configured for facing the superior and inferior articular processes 20, 22 of the facet joint 28. The relative configuration of the superior surface 118 and inferior surface 120 can vary, depending upon the relative position desired between the two adjacent articular processes 20, 22, the anatomical shape of the articular processes 20, 22, ease of insertion of the spacer 114 and other factors. For example, if a neutral alignment is desired between two articular processes 20, 22, the superior and inferior surfaces 118, 120 can have generally parallel planar orientations. If a non-neutral alignment is desired, the superior and inferior surfaces 118, 120 can have a wedge-like relationship to allow fixation of the articular processes 20, 22 in the desired non-neutral position. The height of the spacer 114 at any section between the superior and inferior surfaces 118, 120 can be further configured to accommodate degenerative changes or anatomical anomalies to provide fixation in the desired relative position. Likewise, the lateral sides 122, 124 of the spacer 114 can be generally mirror-images. In other embodiments, the lateral sides 122, 124 are generally parallel. In some embodiments, the lateral sides 122, 124 of the spacer 114 taper inward with increasing distance from the posterior side 116 of the spacer 114. A tapered configuration can facilitate insertion of the spacer 114 into the facet joint 28. In other embodiments, the one or more lateral sides 122, 124 can flare distally or have both tapering and flaring portions.

FIGS. 8A through 8B illustrate an embodiment comprising a spacer 114 with one or more holes 152 between the superior and inferior surfaces 118, 120. In some embodiments, the spacer 114 has one or more holes 152 between the lateral sides 122, 124. The holes 152 can allow bony growth into the spacer 114. The holes 152 can also be filled with graft materials (not shown). The graft material can be an autograft, allograft, xenograft or synthetic material. Synthetic graft material can be ceramic-based, silicon-based or calcium-based. The graft material can also include osteoinductive factors to promote bone ingrowth. One skilled in the art will appreciate that there are many varieties of synthetic graft materials and constituents that can be used between or about the bone segments.

One or more surfaces of the spacer 114 can also have surface projections, indentations, or holes or pores that can further alter the characteristics of the spacer 114. In some embodiments, angled projections, barbs, teeth or ramped surfaces can be provided on one or more surfaces that allow insertion of the spacer 114 in one direction but resist movement in the opposite direction. These ramped surfaces can incline outwardly from one or more spacer surfaces, with a smaller end toward the anterior side 126 and a larger end toward the posterior side 116. These ramped surfaces can be advantageous in reducing the migration of the spacer 114 out of the facet joint 28. Improved fixation of the spacer 114 can maintain the position of the spacer 114 during drilling of the screw holes into the articular processes, for instance when securing the spacer 114 and/or the fixation plate 102. Improved fixation of the spacer 114 can also reduce the forces acting upon the screws or other retaining structures, thereby reducing the risk of back-out. The ramped surfaces are preferably provided on the superior and/or inferior surfaces 118, 120 of the spacer 114, but other surfaces can also have ramped surfaces or other tissue engagement structures. In some embodiments, the tissue engagement structures can be combined with indentations, holes or pores for allowing bony ingrowth or filling with bony matrix or graft materials as described herein. This bony ingrown can enhance insertion and stabilization of the spacer 114.

The spacer 114 can be manufactured from any of a variety of materials known in the art, including but not limited to a polymer such as polyetheretherketone (PEEK), polyetherketoneketone (PEKK), polyethylene, fluoropolymer, hydrogel, or elastomer; a ceramic such as zirconia, alumina, or silicon nitride; a metal such as titanium, titanium alloy, cobalt chromium or stainless steel; or any combination of the above materials.

The spacer 114 can include, be made of, treated, coated, filled, used in combination with, or contain artificial or naturally occurring materials suitable for implantation in the human spine. These materials can include any source of osteogenesis, bone growth-promoting materials, bone derived substances, bone morphogenetic proteins, hydroxyapatite, genes coding for the production of bone, and bone including, but not limited to, cortical bone.

The spacer 114 can also be formed at least in part of material such as metal including, but not limited to, titanium and its alloys, surgical grade plastics, plastic composites, ceramics, or other materials suitable for use as a spinal fusion implant. In some embodiments, the spacer 114 can comprise a radiolucent material, a radio-opaque material, or a combination thereof. A material that is partially or completely radiolucent can be advantageous when evaluating the effect of the spacer 114 post-implantation. Many existing spinal fixation plates and/or spacers obscure visualization of the vertebrae, which can complicate post-operative treatment, diagnosis and prognosis of the patient's condition.

The spacer 114 can include at least in part materials that are bioabsorbable in the body. The spacer 114 can be formed of a porous material or can be formed of a material that intrinsically participates in the growth of bone from one of adjacent vertebral bodies to the other of adjacent vertebral bodies. The spacer 114 can be treated with, coated with, or used in combination with substances to inhibit scar tissue formation. The spacer 114 can be modified, or used in combination with materials to provide antibacterial properties, such as, but not limited to, electroplating or plasma spraying with silver ions or other substance. The spacer 114 can optionally comprise an electrical source to provide ionophoresis of the silver ions into the surrounding tissue to prevent infection. The antibacterial properties can include bactericidal and/or bacteriostatic characteristics. Similarly, anti-fungal characteristics can also be provided. Any of these materials as appropriate can be used at any time after the spacer 114 is inserted.

2. Fixation Plate

In some embodiments, the fixation plate 102 can have an upper portion 104 and a lower portion 106. In use, the upper portion 104 can be adjacent the superior articular process 20 and the lower portion 106 can be adjacent the inferior articular process 22. The upper portion 104 and the lower portion 106 can span the facet joint 28. Other configurations are contemplated.

The fixation plate 102 can have a bone facing surface 108 and an access surface 110. In use, the bone facing surface 108 can contact the surface of one or both articular processes 20, 22 forming the facet joint 28. In some embodiments, other structures or components can lie in between the bone facing surface 108 and the bone surface. The components can include graft materials (not shown). The graft material can be an autograft, allograft, xenograft or synthetic material. Synthetic graft material can be ceramic-based, silicon-based or calcium-based. The graft material can also include osteoinductive factors to promote bone ingrowth. One skilled in the art will appreciate that there are many varieties of synthetic graft materials and constituents that can be used between or about the bone portions.

In some embodiments, the fixation plate 102 can be shaped based upon the anatomical shape of the articular processes 20, 22. The fixation plate 102 can have a generally flat configuration, curved configuration or combination thereof. For instance, the upper portion 104 can be flat or substantially flat and the lower portion 106 can be curved or substantially curved. The upper and the lower portions 104, 106 can be concave or convex. For instance, the upper portion 104 can be concave and the lower portion 106 can be convex. The fixation plate 102 can be generally semi-circular. In some embodiments, the fixation plate 102 can comprise a portion of a circle (e.g., 90°, 100°, 110°, 120°, 130°, 140°, 150°, 160°, 170°, 180°, 190°, 200°, 210°, 220°, 230°, 240°, 250°, 260°, 270°, etc.). In some embodiments, the upper portion 104 of the fixation plate 102 can comprise a portion of a circle (e.g., 10°, 20°, 30°, 40°, 50°, 60°, 70°, 80°, 90°, 100°, 110°, 120°, 130°, 140°, 150°, 160°, 170°, 180°, etc.). In some embodiments, the lower portion 106 of the fixation plate 102 can comprise a portion of a circle (e.g., 10°, 20°, 30°, 40°, 50°, 60°, 70°, 80°, 90°, 100°, 110°, 120°, 130°, 140°, 150°, 160°, 170°, 180°, etc.). In some embodiments, the fixation plate 102 can comprise a portion of a sphere. The fixation plate 102 can be generally shaped to fit the facet joint anatomy. The fixation plate 102 can be dimensioned to allow stable attachment of the fixation plate to the adjacent articular processes 20, 22.

Optionally, each surface of the fixation plate 102 can have a generally flat or curved configuration or combination thereof. Each surface of the fixation plate need not have the same configuration. For instance, the bone facing surface 108 can match or substantially match the anatomical shape of the articular processes 20, 22. The access surface 110 can have the same shape as the bone facing surface 108. In some embodiments, the access surface 110 can have a different shape than the bone facing surface 108. The access surface 110 can be flat while the bone facing surface 108 can be curved.

In some embodiments, the average thickness of the fixation plate 102 can be within the range of about 1 mm to about 5 mm. In other embodiments, the average thickness of the fixation plate 102 can be within the range of about 1.5 mm to about 3.0 mm. The thicknesses of the fixation plate 102 need not be uniform. For instance, the interface between the upper portion 104 and the lower portion 106 can be greater. In other embodiments, the one or more edges of the fixation plate 102 can have a greater thickness creating a flange. For instance, the two lateral edges of the fixation plate 102 can have a greater thickness. The two lateral edges can be dimensioned such that the flange extends about 2 mm beyond the edges of the posterior side 116 of the spacer 114. In some embodiments, the fixation plate 102 can be dimensioned to extend generally about 1 mm to about 20 mm beyond the perimeter of the spacer 114 at the lateral edges. In other embodiments, the flange can extend by 3 mm or 4 mm or more beyond the spacer 114 at the lateral edges. The flange may or may not extend uniformly along the fixation plate 102. The flange of the fixation plate 102 can optionally be rounded, smoothed or polished.

In some embodiments, illustrated in FIGS. 8A through 8B, the fixation plate 102 can have a general square or rectangular shape. In other embodiments, the fixation plate 102 can comprise any of a variety of other shapes, including trapezoids, circles, ovals, polygons or other closed shapes. The corners where any two sides of the fixation plate 102 meet can be angled, rounded or curved. The fixation plate 102 depicted in FIGS. 8A through 8B can comprise rounded corners. The fixation plate 102 may or may not have a symmetrical configuration with respect to the upper and lower portions 104, 106. The fixation plate 102 may or may not have a symmetrical configuration with respect to the left and right portions of the fixation plate 102.

In some embodiments, the fixation plate 102 can be conformable to the articular processes 20, 22 of the implantation site. In some embodiments, the fixation plate 102 is configured to provide an improved fit with the articular processes 20, 22. For example, in some embodiments, the fixation plate 102 has a bend, angle or curve to generally match the natural shape of one or more articular processes 20, 22. The fixation plate 102 may be rigid with a preformed bend. Alternatively, the fixation plate 102 may be sufficiently malleable that it will conform post implantation to the unique configuration of one or more articular processes 20, 22. In some embodiments, the fixation plate has one or more hinges, such as between the upper and lower portions 104, 106, that can bend to conform the fixation plate to the shape of the articular processes 20, 22. In some embodiments, the fixation plate 102 is shaped to overlie the facet joint 28. The fixation plate 102 shaped to cover a portion of the joint capsule of the facet joint 28.

The fixation plate 102 can be made from a material that is the same or different from the spacer 114. In some embodiments, the fixation plate 102 and the spacer 114 having different materials can be beneficial. For instance, the spacer 114 can be configured to withstand compressive forces while the fixation plate 102 can be configured to withstand primarily tension forces based on different material selection. The fixation plate 102 can comprise a polymer, a woven material, or a combination thereof.

The fixation plate 102 can be manufactured from any of a variety of materials known in the art, including but not limited to a polymer such as polyetheretherketone (PEEK), polyetherketoneketone (PEKK), polyethylene, fluoropolymer, hydrogel, or elastomer; a ceramic such as zirconia, alumina, or silicon nitride; a metal such as titanium, titanium alloy, cobalt chromium or stainless steel; or any combination of the above materials. The fixation plate 102 can include, be made of, treated, coated, filled, used in combination with, or contain artificial or naturally occurring materials suitable for implantation in the human spine. These materials can include any source of osteogenesis, bone growth-promoting materials, bone derived substances, bone morphogenetic proteins, hydroxyapatite, genes coding for the production of bone, and bone including, but not limited to, cortical bone.

The fixation plate 102 can also be formed of material such as metal including, but not limited to, titanium and its alloys, surgical grade plastics, plastic composites, ceramics, or other materials suitable for use as a spinal fusion implant. In some embodiments, the fixation plate 102 can comprise a radiolucent material, a radio-opaque material, or a combination thereof. A material that is partially or completely radiolucent can be advantageous when evaluating the effect of the fixation plate 102 post-implantation.

In some embodiments, the fixation plate 102 is a solid structure. In some embodiments, the fixation plate 102 comprises a mesh or lattice. The fixation plate 102 can include at least in part materials that are bioabsorbable in the body. The fixation plate 102 of the described embodiments can be formed of a porous material or can be formed of a material that intrinsically participates in the growth of bone from one of adjacent vertebral bodies to the other of adjacent vertebral bodies. The fixation plate 102 can be treated with, coated with, or used in combination with substances to inhibit scar tissue formation. The fixation plate 102 can be modified, or used in combination with materials to provide antibacterial properties, such as, but not limited to, electroplating or plasma spraying with silver ions or other substance. The fixation plate 102 can optionally comprise an electrical source to provide ionophoresis of the silver ions into the surrounding tissue to prevent infection. The antibacterial properties can include bactericidal and/or bacteriostatic characteristics. Similarly, anti-fungal characteristics can also be provided.

In some embodiments, the fixation plate 102 can be configured for positioning across a facet joint 28 such that the upper portion 104 of the fixation plate 102 can contact the superior articular process 20 and the lower portion 106 of the fixation plate 102 can contact the inferior articular process 22. In some embodiments, the fixation plate 102 can span two articular processes 20, 22 of the facet joint 28. In some embodiments, the fixation plate 102 can contact a single articular process of the facet joint 28. In such embodiments, the fixation plate 102 can contact only the superior articular process 20 or contact only the inferior articular process 22. In some embodiments, the fixation plate 102 can be configured to contact other vertebral structures such as the pedicles, transverse processes, vertebral bodies, and spinous processes. In some embodiments, the fixation plate 102 can be configured to attach to these vertebral structures without attaching or contacting the articular processes 20, 22.

In some embodiments, the upper portion 104, the lower portion 106, or both the upper portion 104 and the lower portion 106 can have one or more holes 112 oriented between the bone facing surface 108 and the access surface 110. In some embodiments, these holes 112 are sized to accept screws and/or other attachment devices for anchoring the fixation plate 102 to the vertebral bone. In some embodiment, these holes are sized to accept adhesive, medication or bone grafts. In other embodiments, other fixations devices are utilized, as will be described herein.

Each hole 112 of the fixation plate 102 need not have the same configuration or size. The holes 112 can be round in cross-section or any other cross-sectional shape. In some embodiments, at least a portion of the hole 112 can have a non-round cross-section, such as an oval, square, rectangle, polygon or other closed shape. The holes 112 can be dimensioned to allow passage of a portion of a fixation device there through (e.g., body) while resisting passage of a portion of the fixation device (e.g., head) completely through the hole 112. The inside surface of the holes 112 can be covered with a lubricious coating to facilitate insertion and/or movement of the fixation device through the hole 112. The hole 112 can form an angle with the longitudinal axis of the fixation plate 102. In some embodiments, the hole 112 is substantially perpendicular or perpendicular to the fixation plate 102. In some embodiments, the through axis of the hole 112 is perpendicular the longitudinal axis of the to the fixation plate 102. In some embodiments, the angle is acute (e.g., 5°, 10°, 15°, 20°, 25°, 30°, 35°, 40°, 45°, 50°, 55°, 60°, 65°, 70°, 75°, 80°, 85°, etc.) The hole 112 can form an angle with the longitudinal axis of the spacer 114. In some embodiments, the through axis of the hole 112 is parallel or substantially parallel to the longitudinal axis of the spacer 114. In some embodiments, the angle is acute (e.g., 5°, 10°, 15°, 20°, 25°, 30°, 35°, 40°, 45°, 50°, 55°, 60°, 65°, 70°, 75°, 80°, 85°, etc.) The through axis of the hole 112 can point toward or away from the spacer 114. The through axis of the hole 112 can point toward or away from the facet joint 28.

In some embodiments, the fixation plate 102 comprises at least one hole 112 in the upper portion 104. In some embodiments, the fixation plate 102 comprises at least one hole 112 in the lower portion 106. In some embodiments, the fixation plate 102 comprises at least one hole 112 in the upper portion 104 and at least one hole 112 in the lower portion 106. In some embodiments, the hole 112 in the upper portion 104 is angled to guide the fixation device into the superior articular process 20. In some embodiments, the hole 112 in the lower portion 106 is angled to guide the fixation device into the inferior articular process 22. In some embodiments, the hole 112 in the upper portion 104 and/or the lower portion 106 is angled to guide the fixation device away from the facet joint 28.

As shown in FIGS. 8A and 8B, the spacer 114 and the fixation plate 102 can be separate components. This arrangement may allow for a greater ability to position the components of the implant 100 relative to the facet joint 28. In some embodiments, the spacer 114 and the fixation plate 102 are integrally formed. The spacer 114 and the fixation plate 102 can be monolithically formed, for instance of the same material. In other embodiments, an adhesive can join the spacer 114 and the fixation plate 102. In some embodiments, the spacer 114 and the fixation plate 102 can be coupled to allow movement there between as described herein.

C. Hinge

In some embodiments, the spacer 114 and the fixation plate 102 can be configured to provide some degree of relative movement between each other. By providing some relative movement between the spacer 114 and the fixation plate 102, the implant 100 can have improved securement to osseous structures with improved conformance to the existing anatomy at the site of implantation. FIGS. 9A through 9D depict an embodiment comprising a hinge joint 128 oriented to allow pivoting of the fixation plate 102 relative to the spacer 114. In the illustrated embodiment, the hinge joint 128 is oriented to allow pivoting of the fixation plate 102 relative to the posterior side 116. In other embodiments, the hinge joint 128 can be oriented to allow pivoting relative to other portions of the spacer 114, including the superior surface 118, the inferior surface 120, and the lateral sides 122, 124. The hinge joint 128 can permit movement in any plane, including the sagittal plane, transverse plane, coronal plane, or any plane in between the three planes.

In the illustrated embodiment, the posterior side 116 supports a pivot 130. In some embodiments, the pivot 130 is located in a symmetric position on the spacer 114. The pivot 130 can be located between the superior and inferior surfaces 118, 120 of the spacer 114. In other embodiments, the pivot 130 is located in an eccentric location on the spacer 114. In the illustrated embodiment, the posterior side 116 is coupled to the pivot 130 at a mid-point along the length of the spacer 114. The pivot 130 can extend along the entire length of the spacer 114 or a portion thereof. For instance, the pivot 130 can extend along a portion of the total length, the entire length or a greater length than the spacer 114.

The fixation plate 102 comprises one or more barrels 132 shaped to rotate about the pivot 130. In the illustrated embodiment, the fixation plate 102 comprises two barrels 132 on either end of the pivot 130. The barrels 132 can be any shape which allows rotational movement about the pivot 130. In the illustrated embodiment, the barrels 132 are substantially cylindrical or cylindrical. In other embodiments, the barrels 132 comprise a portion of a cylinder. In some embodiments, the barrels 132 are located in a symmetric position on the fixation plate 102. For instance, the barrels 132 can be located between the upper and lower portions 104, 106 of the fixation plate 102.

In some embodiments, only the upper portion 104 of the fixation plate 102 is provided. The upper portion 104 of the fixation plate 102 can be secured to the superior articular process 20. The one or more barrels 132 can be located near one end of the upper portion 104. The one or more holes 112 can be located near the other end of the upper portion 104. This may be beneficial if the inferior articular process is severely curved. Other configurations are possible. In some embodiments, only the lower portion 106 of the fixation plate 102 is provided. The lower portion 106 of the fixation plate 102 can be secured to the inferior articular process 22. The one or more barrels 132 can be located near one end of the lower portion 106 and the one or more holes 112 can be located near the other end of the lower portion 106.

The hinge joint 128 provided between the spacer 114 and the fixation plate 102 can be further configured to limit the range of movement provided. For instance, the pivot 130 or the barrels 132 can be shaped to limit the range of motion.

In other embodiments, the range of motion is limited by the abutment of the fixation plate 102 and the anatomy or the abutment of the fixation plate 102 and the spacer 114. The spacer 114 and/or fixation plate 102 can be designed to improve the range of motion. For instance, the fixation plate 102 can include recesses on the bone facing surface 108 to provide clearance for the spacer 114 or the anatomy. The spacer 114, or a portion thereof such as the posterior side 116 of the spacer 114, can be reduced in size or tapered to provide clearance for the fixation plate 102. Other configurations are contemplated to allow greater range of movement between the fixation plate 102 and the spacer 114.

Although a hinge-type movement joint is depicted in FIGS. 9A to 9D, other types of joints or connections between the spacer 114 and fixation plate 102 are also contemplated, including but not limited to an elastomeric joint, a ball-and-socket joint, a sliding joint, a rotatable articulation configured to allow reversible separation of the fixation plate 102 and the spacer 114, or one or more metallic cords embedded or attached between the fixation plate 102 and spacer 114 to allow limited polyaxial movement. One of skill in the art will understand that the hinge joint 128 may be configured to vary other characteristics of the hinge joint, including frictional resistance or ratchet-type resistance to movement.

Moreover, although the spacer 114, the fixation plate 102 and a single hinge joint 128 are depicted, other embodiments can have two or more movement joints. The movement joints can be the same or different types. In some embodiments, the fixation plate 102 can be divided into two plates. For instance, the upper and the lower portion 104, 106 can separate plates. Each of the upper and lower portion 104, 106 can include one or more barrels 132 which independently move or pivot relative to the spacer 114 to provide additional conformance to the existing anatomy.

In some embodiments, the fixation plate 102 can be configured with two or more subcomponents that are provided with an intra-component hinge or movement joint to provide better conformance of the fixation plate 102 to the existing anatomy. For instance, the upper portion 104 of the fixation plate 102 can be divided into two plates. The two plates of the upper portion 104 can be joined by an intra-component hinge such that the two plates of the upper portion 104 can pivot relative to each other. Each of the two plates of the upper portion 104 can independently move or pivot relative to each other to provide additional conformance to the existing anatomy.

In some embodiments, the spacer 114 can be configured with two or more subcomponents that are provided with an intra-component hinge or movement joint to provide better conformance of the spacer 114 to the existing anatomy. For instance, the spacer 114 can have superior and inferior subcomponents with an intra-component hinge joint to allow pivoting of the superior and inferior surfaces 118, 120 of the spacer 114. Depending on the orientation of this intra-component hinge joint, the superior and inferior surfaces of the spacer 114 can pivot laterally in a superior-inferior direction, or in any direction in-between.

D. Multi-Axial Movement

FIGS. 10A through 10D illustrate an implant 200 comprising a spacer 214 and a fixation plate 202. The spacer 214 can have any of the features described above with respect to the spacer 114. The fixation plate 202 can have any of the features described above with respect to the fixation plate 102. In some embodiments, multiple joints between the spacer 214 and the fixation plate 202 can be configured to provide additional degrees of movement. By providing adjustment of the fixation plate 202 in multiple degrees of movement relative to the spacer 114, securement to osseous structures can be improved while also improving conformance to the existing anatomy at the site of implantation.

Figure 10A:
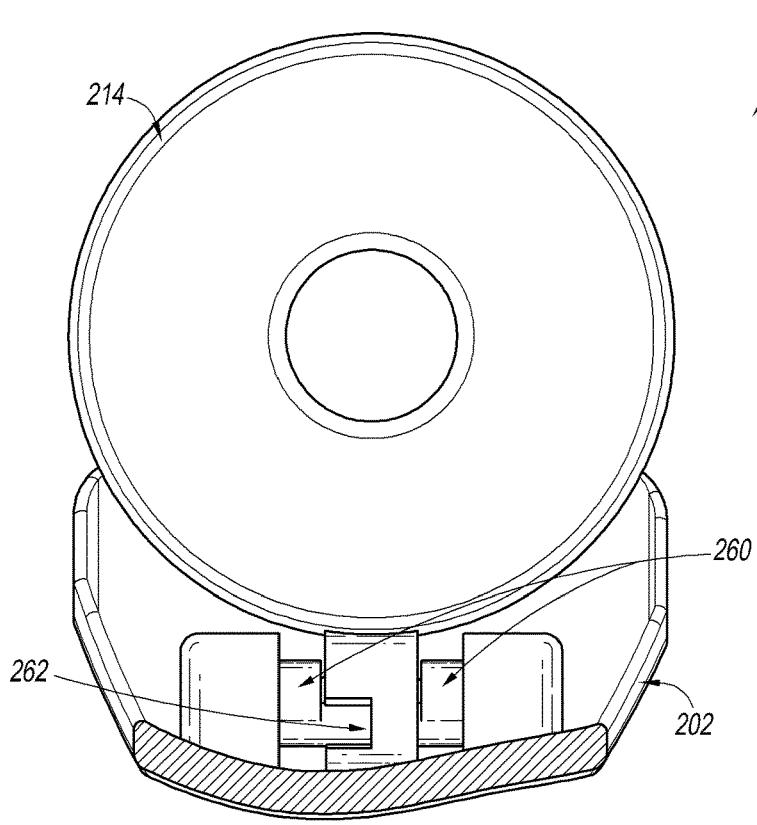
FIGS. 10A to 10D are various views of an embodiment of an implant comprising a pivoting fixation plate with at least two articulations and spacer.
Figure 10B:
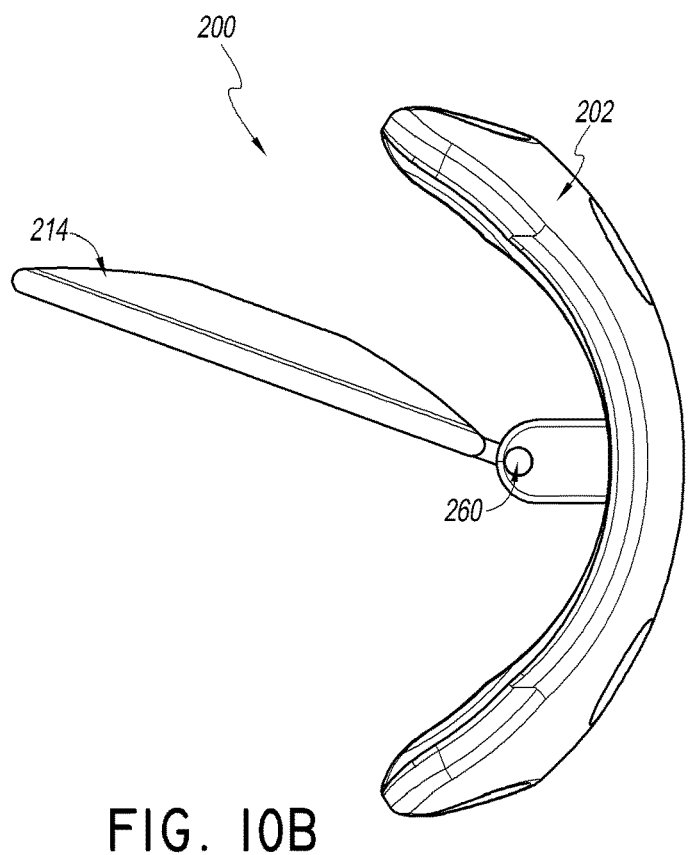
Figure 10C:
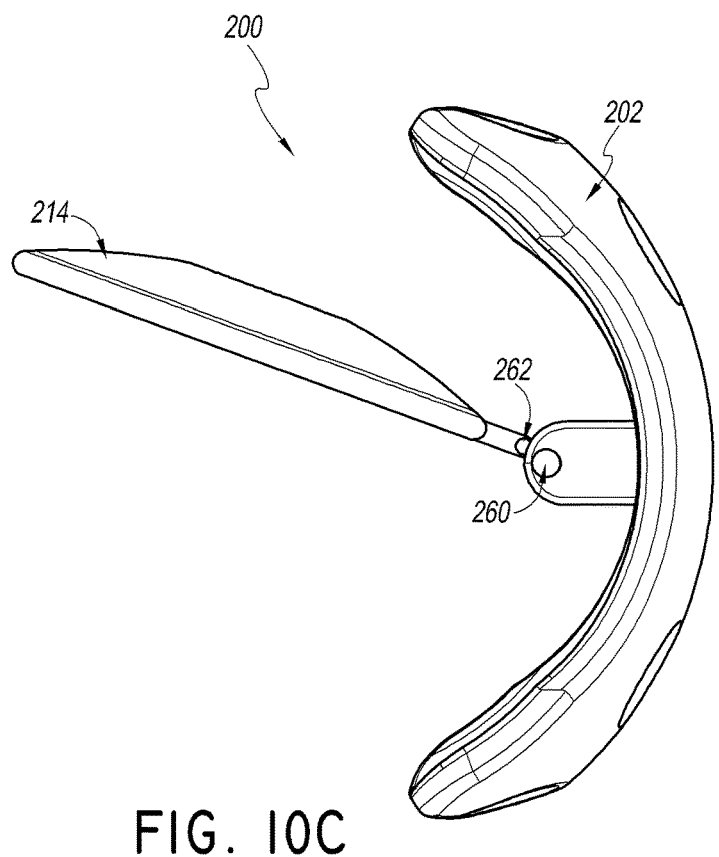
Figure 10D:
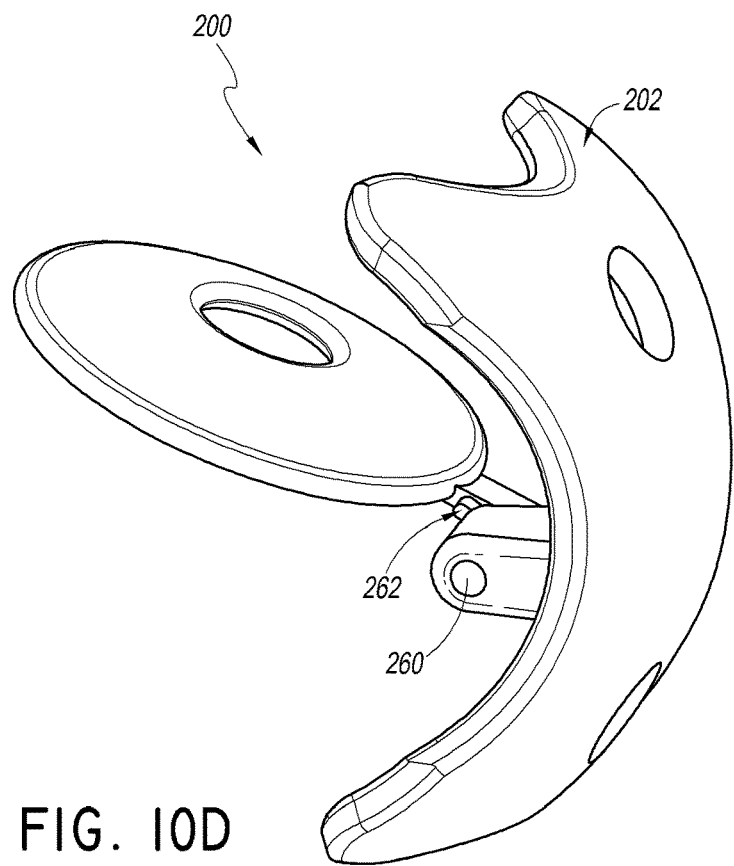
Figure 10E:
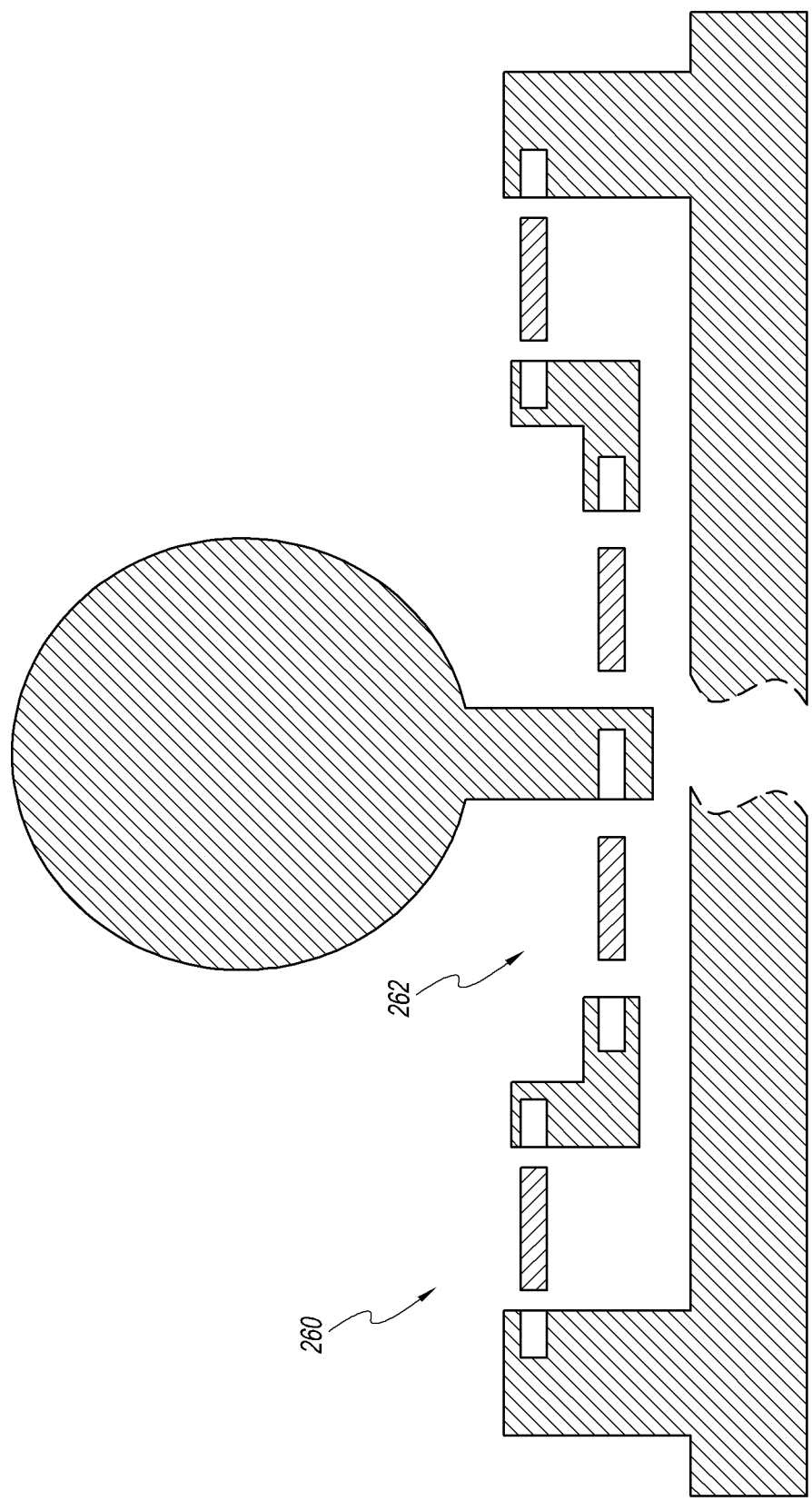
FIG. 10E is a schematic exploded view of the implant of FIG. 10A.

FIGS. 10A through 10D illustrate an implant 200 comprising a double hinge joint 260 and single hinge joint 262 disposed to allow multiple degrees of movement. The double hinge joint 260 can move in a circular cam motion about the longitudinal axis of single hinge joint 262. In an alternative description, the single hinge joint 262 can move in a circular cam motion about the longitudinal axis of the double hinge joint 260. The two hinge configuration can allow the spacer 214 and the fixation plate 202 to move in a circular and reciprocating movement relative to each other. The combination of the double hinge joint 260 and the single hinge joint 262 can permit the relative movement in two directions, the directions dependent upon the orientation of the spacer 114 and the facet joint 28. Both the spacer 214 and the fixation plate 202 can also have an additional degree of pivotal movement about the hinge joints 260 and 262. FIGS. 10A and 10B illustrate the implant 200 in the configuration where the distance between the spacer 214 and the fixation plate 202 is at its minimum. FIGS. 10C and 10D illustrate the implant 200 in the configuration where the distance between the spacer 214 and the fixation plate 202 is toward its maximum. FIG. 10E illustrates a schematic exploded view of the implant 200. As shown, the double joint 260 and the single hinge joint 262 each have a respective axis. The fixation plate 202 can move in a circular path about the axis of the double hinge joint 260. The fixation plate 202 can move in a circular path about the axis single hinge joint 262. The fixation plate 202 can move in additional paths of motion by the combination of the double hinge joint 260 and the single hinge joint 262.

In some embodiments, the hinge joints 260 and 262 can be oriented to allow similar movements in any plane such as the sagittal plane, transverse plane, coronal plane, or any plane in-between the three planes. In some embodiments, the hinge joints 260 and 262 provided between the spacer 214 and the fixation plate 202 can be configured to limit the range of movement provided. For instance, the movement joints including the barrels and/or pivots can limit the range of motion. In some embodiments, the range of motion can be limited by the fixation plate 202 abutting the spacer 114 or the anatomy. In some embodiments, recesses in the fixation plate 202 or a size reduction or tapering of the spacer 214 about the hinge joints 260 and 262 can allow greater range of motion. In FIGS. 10A through 10D, the hinge joints 260, 262 are depicted in a symmetric position on the spacer 214 and fixation plate 202. In other embodiments, the hinge joints 260, 262 are located at an eccentric location on the spacer 214 and/or the fixation plate 202.

Although hinge-type movement joints are depicted in FIGS. 10A through 10D, other types of joints or connections between the spacer 214 and fixation plate 202 are also contemplated, including but not limited to elastomeric joints, ball-and-socket joints, sliding joints, rotatable articulations configured to allow reversible separation of the fixation plate and the spacer, or one or more metallic cords embedded or attached between the fixation plate and spacer to allow limited polyaxial movement. The hinge joints 260 and 262 can be configured to vary other characteristics of the movement joints, including frictional resistance or ratchet-type resistance to movement.

The hinge-type movement joints depicted in FIGS. 10A through 10D can advantageously allow the distance between the fixation plate 202 and the spacer 214 to be adjusted by the surgeon. In this manner, a single implant 200 can be adapted to individual anatomies. This can reduce the amount of inventory needed.

In some embodiments, the fixation plate 202 comprises at least one hole 212 in the upper portion 204. In some embodiments, the fixation plate 202 can comprise at least one hole 212 in the lower portion 206. In some embodiments, the fixation plate 202 can comprise at least one hole 212 in the upper portion 204 and at least one hole 212 in the lower portion 206. The one or more holes 212 can allow the passage of one or more fixation devices to secure the fixation plate 202 to the anatomy.

E. Multiple Pivot Plates

FIGS. 11A through 11D illustrate an implant 400 comprising a spacer 414. The spacer 414 can have any of the features described above with respect to the spacer 114 or 214. The implant 400 comprises two or more fixation plates 470, 472. The fixation plates 470, 472 can have any of the features described above with respect to the fixation plate 102 or 202. In some embodiments, the implant 400 can comprise two or more fixation plates 470, 472 with independent movement joints, wherein each fixation plate 470, 472 is coupled to a separate movement joint that can independently move or pivot to provide additional conformance to the existing anatomy.

FIGS. 11A through 11D depict the implant 400, comprising the spacer 414, a first fixation plate 470 coupled to the spacer 414 by a first hinge joint 464, and a second fixation plate 472 coupled to the spacer 414 by a second hinge joint 466. The hinge joints 464 and 466 can allow the pivotal movement between the spacer 414 and the two fixation plates 470 and 472, respectively.

In the illustrated embodiment, the spacer 414 supports a pivot 430. In the illustrated embodiment, the spacer 414 supports the pivot along the length of the pivot 430, for instance at a midpoint. The pivot 430 can extend along the entire length of the spacer 414 or a portion thereof. For instance, the pivot 430 can be a portion of the total length, the entire length or a greater length than the spacer 414. In some embodiments, the pivot 430 is located in a symmetric position on the spacer 414. In other embodiments, the pivot 430 is located in an eccentric location on the spacer 414.

The fixation plates 470, 472 each comprises one more barrels 432 configured to rotation about the pivot 430. The barrels 432 can be any shape which allows rotational movement about the pivot 430. In the illustrated embodiment, the barrels 432 are substantially cylindrical or cylindrical. In other embodiments, the barrels 432 comprise a portion of a cylinder. The fixation plates 470, 472 are mounted via the barrels 432 on either end of the pivot 430. In some embodiments, the barrels 432 are located in an eccentric location on the fixation plate 470, 472. For instance, the barrels 432 can be located near one end of the fixation plates 470, 472. In other embodiments, the barrels 432 are located on a symmetric position on the fixation plates 470, 472. The pivot 430 can include stops 434 on either end of the pivot 430. The stops 434 can prevent the barrels 432 from disengaging the pivot 430.

The hinge joints 464 and 466 provided between the spacer 414 and the fixation plates 470, 472 can be further configured to limit the range of movement provided. In some embodiments, the hinge joints 464 and 466 themselves limit the range of motion. For instance, the pivot 430, the barrels 432 and/or the stops 434 can be shaped to limit the range of motion. In other embodiments, the range of motion is limited by the abutment of the fixation plates 470, 472 and the anatomy or the abutment of the fixation plates 470, 472 and the spacer 414. The spacer 414 and/or fixation plates 470, 472 can be designed to improve the range of motion. For instance, the fixation plates 470, 472 can include recesses on the bone facing surface to provide clearance for the spacer 414 or the anatomy. The spacer 414, or portion thereof, can be reduced in size or tapered to provide clearance for the fixation plates 470, 472. Other configurations are contemplated to allow greater range of movement between the fixation plates 470, 472 and the spacer 414.

Although a hinge-type movement joint is depicted in FIGS. 11A through 11D, other types of joints or connections between the spacer 414 and fixation plates 470, 472 are also contemplated, including but not limited to an elastomeric joint, a ball-and-socket joint, a sliding joint, a rotatable articulation configured to allow reversible separation of the fixation plates 470, 472 and spacer 414, or one or more metallic cords embedded or attached between the fixation plates 470, 472 and spacer 414 to allow limited polyaxial movement. One of skill in the art will understand that the hinge joints 464, 466 may be configured to vary other characteristics of the hinge joints, including frictional resistance or ratchet-type resistance to movement. In some embodiments, the hinge joints 464 and 466 can each comprise multiple joints to provide multi-axial motion, as described herein.

Moreover, although a single spacer 414 and a single pivot 430 are depicted, other embodiments can have two or more pivots 430. In some embodiments, the spacer 414 can have a split configuration so that each portion has a separate pivot with an independent pivot axis. The fixation plates 470, 472 can independently move or pivot about these independent pivot axes to provide additional conformance to the existing anatomy. The hinge joints 464 and 466 can be oriented to allow pivoting in any plane such as the sagittal plane, transverse plane, coronal plane, or any plane in-between the three planes. For instance, the one or more pivots 430 can be oriented with respect to the spacer 414 to allow movement in any plane.

In some embodiments, each fixation plates 470, 472 can be configured with two or more subcomponents that are provided with an intra-component hinge to provide better conformance of the fixation plate to the existing anatomy. For instance, the fixation plate 470 can be divided into two separate plates. The separate plates can be joined by an intra-component hinge such that the separate plates can pivot relative to each other. Each of the separate plates can independently move or pivot relative to each other to provide additional conformance to the existing anatomy.

In the illustrated embodiment, the fixation plates 470 and 472 are mounted on the pivot 430 in different orientations. The fixation plates 470 and 472 are laterally offset. For instance, the fixation plate 470 is generally parallel to the inferior surface 420 as shown in FIG. 11B. The fixation plate 472 is generally parallel to the superior surface 418 as shown in FIG. 11B. In some embodiments, the fixation plates 470 and 472 can be pivoted to a predetermined position, such as generally parallel to the spacer 414, so that the spacer 414 can present a low profile, as illustrated in FIGS. 11A and 11B. This configuration can be advantageous for insertion of the implant 400 into the body of a patient. In other embodiments (not shown), the fixation plates 470 and 472 are not laterally offset. The fixation plates 470 and 472 are mounted on the pivot 430 in the same orientations. For instance, the fixation plates 470 and 472 can be both parallel to the superior surface 418 in the low profile configuration. For instance, the fixation plates 470 and 472 can be both parallel to the inferior surface 420 in the low profile configuration.

In some embodiments, the fixation plates 470 and 472 can be pivoted so that they extend away from the spacer 414. FIGS. 11C and 11D illustrate the implant 400 in this configuration. This configuration can be advantageous for fixation of the implant 400 to the articular processes 20, 22. In some embodiments, the first fixation plate 470 can be pivoted to a position generally perpendicular to the spacer 414. The first fixation plate 470 can be pivoted to a position generally perpendicular to the superior surface 118. A portion of the first fixation plate 470 can extend across the width of the spacer 414. The second fixation plate 472 can be pivoted to a position generally perpendicular to the spacer 414. The second fixation plate 472 can be pivoted to a position generally perpendicular to the inferior surface 420. A portion of the second fixation plate 472 can extend across the width of the spacer 414. The distal ends of the fixation plates 470 and 472 can shear past each other during pivoting. The fixation plates 470 and 472 can cross. The first fixation plate 470 can be coupled to the superior articular process 20 and the second fixation plate 472 can be coupled to the inferior articular process 22. The second fixation plate 472 can be pivoted in a direction opposite to the first fixation plate 470. In some embodiments, the first and second fixation plates 470, 472 can be independently pivoted to various positions relative to the spacer 414 for coupling with articular processes 20, 22. The range of motion of each fixation plate can be greater than 90 degrees, greater than 180 degrees, greater than 270 degrees, etc. In some embodiments, each fixation plate has nearly 360 degrees of movement. The fixation plates 470 and 472 can pivot to any angle.

In some embodiments, only first fixation plate 470 is provided. The first fixation plate 470 can be secured to the superior articular process 20. This may be beneficial if the inferior articular process 22 is severely curved. In some embodiments, only the second fixation plate 472 is provided. The second fixation plate 472 can be secured to the inferior articular process 22.

In some embodiments, the implant 400 can include more than two fixation plates. Each fixation plate can have a low profile configuration wherein each fixation plate is generally parallel to the spacer 414. Each fixation plate can pivot to a position generally perpendicular to the spacer 414. In some embodiments, each fixation plate pivots to an obtuse angle.

The above described embodiments allow the first fixation plate 470 to lie generally flat on the superior process 20 and the second fixation plate to lie generally flat on the inferior process 22. The second fixation plate 472 can be positioned in generally the opposite direction as the first fixation plate 470.

In some embodiments, the first fixation plate 470 comprises at least one hole 412. In some embodiments, the second fixation plate 472 can comprise at least one hole 412. The holes 412 can be spaced away from the barrels 432. In other embodiments, each fixation plate 470, 472 comprises two or more holes 412. The hole 412 in each fixation plate 470, 472 can allow the passage of one or more fixation devices to secure the fixation plates 470, 472 to the anatomy.

F. Angled Screw

Figure 12:
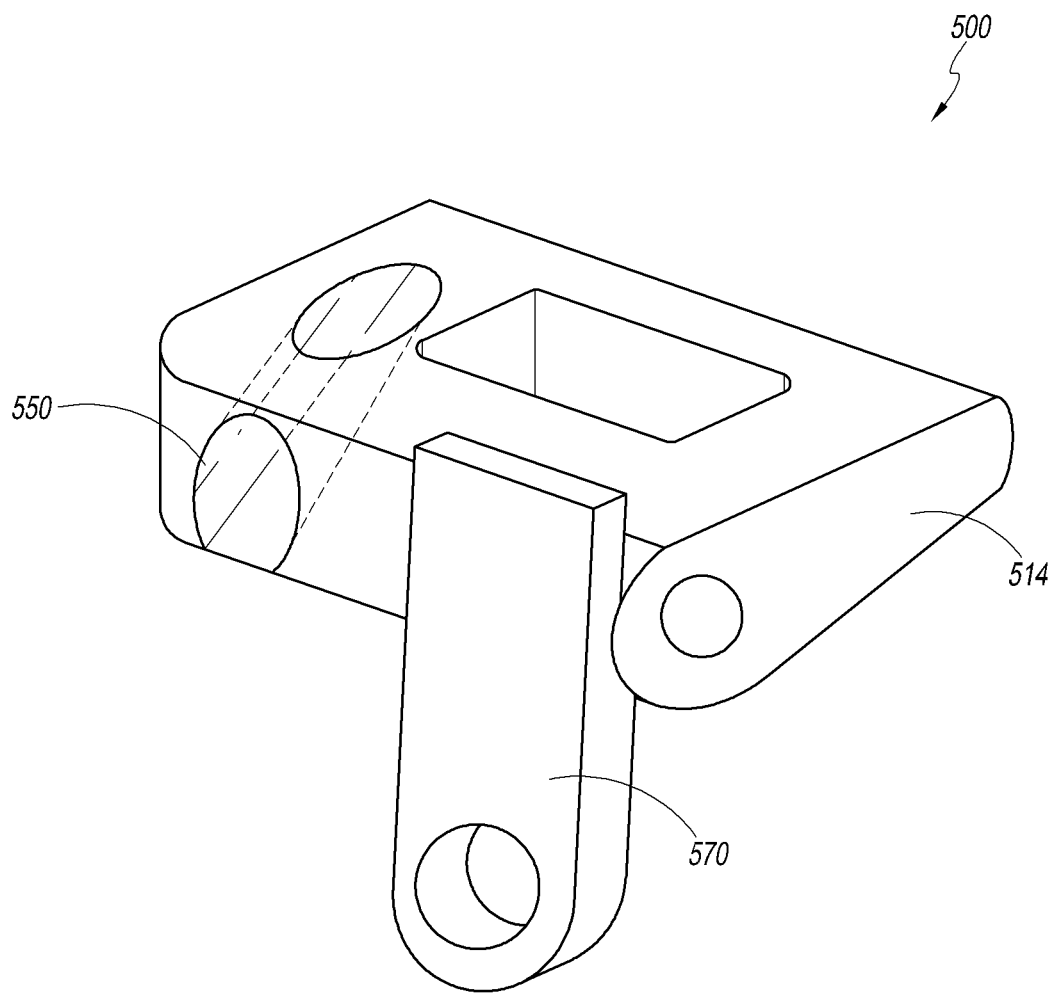
FIG. 12 is a perspective view of an embodiment of an implant comprising a spacer with an angled fixation hole and a pivoting fixation plate.

In some embodiments, the spacer 514 comprises one or more fixation holes 550 between surfaces, as in the illustrated embodiment of FIG. 12. The fixation hole 550 can be a through lumen from a first surface to another surface. The spacer 514 can have a superior surface and an inferior surface, a posterior side and an anterior side, and lateral sides, similar to implants described above. The fixation hole 550 can extend from the posterior side to any other surface of the implant 514. The spacer 514 can include an axis extending from the posterior side to the anterior side (e.g., a longitudinal axis). The fixation hole 550 can form a first angle with the axis in a plane parallel to the width of the spacer 514. The first angle can direct a fixation device either toward or away from the middle of the spacer 514. In some embodiments, the first angle is about 15°, with the fixation hole 550 extending toward the middle of the spacer 514. In some embodiments, the first angle has a range from 0° with the fixation hole 550 extending parallel to the axis to 45° with the fixation hole 550 extending toward the middle of the spacer 514. In some embodiments, the first angle has a range from −30° (e.g., with the fixation hole 550 extending 30° away from the middle of the spacer 514) to 60° (e.g., with the fixation hole 550 extending 60° toward the middle of the spacer 514).

The fixation hole 550 can form a second angle with the axis in a plane parallel to the height of the spacer 514. The second angle can be in a plane perpendicular to the first angle. The second angle is from the horizontal and can be considered an upward/downward angle. In some embodiments, the second angle is about 35°, with the fixation hole 550 extending upward toward the superior vertebra or downward toward the inferior vertebra. In some embodiments, the second angle has a range from 15° to 45° with the fixation hole 550 extending upward or downward. In some embodiments, the second angle has a range from 5° to 75° with the fixation hole 550 extending upward or downward. The spacer 514 can have an increased thickness near the fixation hole 550. The fixation hole 550 can be sized to insert a spacer fixation device therethrough.

To secure the spacer 514 between articular processes, the spacer fixation device can be provided. The spacer fixation device can be similar to the fixation device described herein. The spacer fixation device can be inserted through an angled fixation hole 550. In some embodiments, the distal end of the spacer fixation device can be formed into a sharp tip that can be configured to penetrate the spacer 514 and the adjacent vertebra. The proximal end of the spacer fixation device can be configured to engage a driving instrument. For example, the proximal end may have a portion with hexagonal shape, protruding slot, or threading to engage corresponding driver. Alternatively, the proximal end of the spacer fixation device may have central bore with female threads, internal hex, or any other method of removably coupling to a driver.

The implant 500 can have one or more fixation plates 570 with independent movement joints, wherein each fixation plate 570 is coupled to a separate movement joint that can independently move or pivot to provide additional conformance to the existing anatomy, similar to as described above in other embodiments. The fixation plate 570 can be mounted offset to one side of the spacer 514 with the fixation hole 550 offset to the other side of the spacer 514, as illustrated in FIG. 12. In some embodiments, the fixation plate 570 comprises at least one hole. The hole in the fixation plate 570 can allow the passage of a fixation device to secure the fixation plates 570 to the anatomy.

In the illustrated embodiment, the fixation hole 550 is angled towards a superior vertebra while the fixation plate 570 is configured to couple to an inferior vertebra. However, in other embodiments, the fixation hole 550 can be angled toward an inferior vertebra while the fixation plate 570 is configured to couple to a superior vertebra. The embodiment shown in FIG. 12 can be useful where it is beneficial to fixate the implant 500 with an angled screw to one vertebra and with a fixation plate to the other adjacent vertebra because of restrictions in the patient's anatomy or other reason.

In some embodiments, the spacer fixation device or the fixation device can be formed of a metal such as, for example, titanium or titanium alloy. In some embodiments, the spacer fixation device or the fixation device can comprise a helical and/or corkscrew shaped body or wire with a proximal end and a distal end. The spacer fixation device or the fixation device can be formed in a variety of ways, such as, for example by bending a straight wire or rod into a helical or corkscrew arrangement. In other embodiments, the spacer fixation device or the fixation device is a screw or other anchor. In some embodiments, the spacer fixation device or the fixation device can be machined or otherwise formed. In some embodiments, the spacer fixation device or the fixation device may be made of PEEK or other radiolucent material.

In some embodiments, the spacer fixation device or the fixation device is a helically shaped wire. The helically shaped wire can have certain advantages over traditional fixation screws used within the facet joint. For example, as compared to screws, a pilot hole does not need to be prepared. Accordingly, the procedure can be faster. In addition, less bone is removed from the articular process. The helically shaped wire can also have increased pull out strength as compared to screws.

In some methods of use, the spacer fixation device is inserted into a fixation hole 550 and/or the fixation device is inserted into the hole in the fixation plate 570 prior to insertion into the facet joint. In some embodiments, a pilot hole is used and a drill guide can be used. The pilot hole can guide the spacer fixation device through the fixation hole 550 and/or the fixation device through the hole in the fixation plate 570. Pilot holes in the articular processes may be prepared for the spacer fixation device or the fixation device using a punch. The spacer fixation device or the fixation device may be removably coupled to an inserter for their insertion. The inserter may comprise a handle, and may advance the spacer fixation device or the fixation device by, for example, rotation or impaction of the handle.

G. Demineralized Bone Matrix

Figure 13:
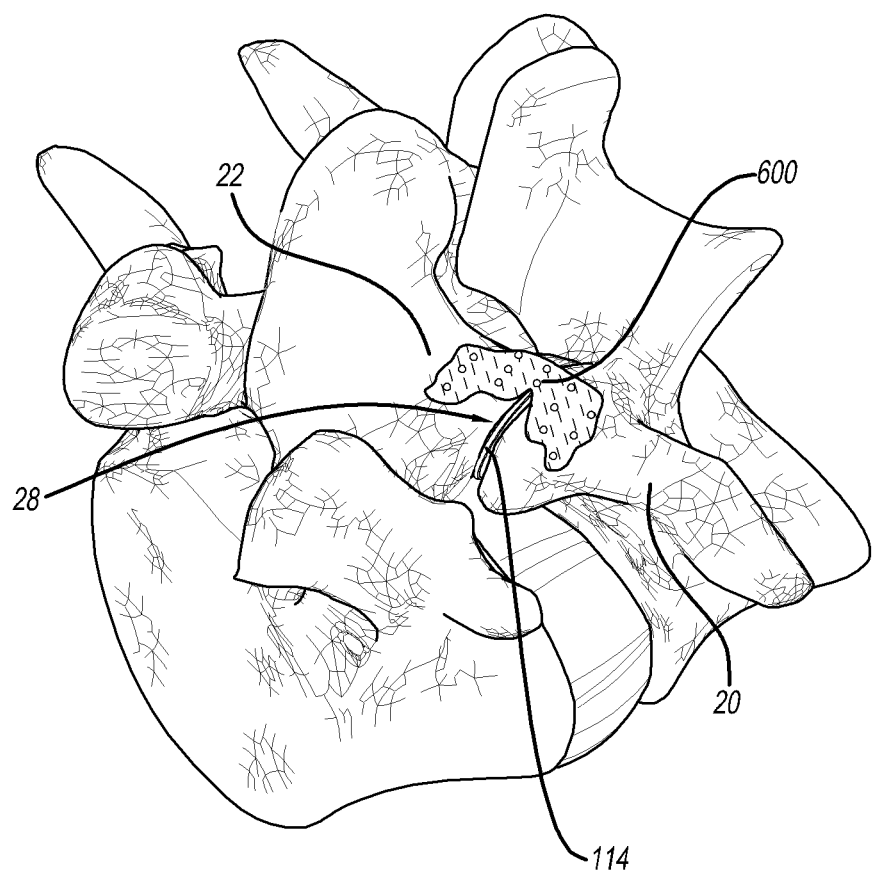
FIG. 13 is a perspective view of an implant inserted into a facet joint and demineralized bone matrix placed over the facet joint.

In some embodiments, the spacer 114 is utilized in combination with allograft or demineralized bone matrix 600, as illustrated in FIG. 13. The spacer 114 may be inserted into the facet joint 28 prior to positioning the demineralized bone matrix 600. The demineralized bone matrix 600 can be utilized instead of the fixation plate 102 described herein. In other embodiments, the demineralized bone matrix is placed between one or more fixation plates 102, 202, 470, 472, 570 and one or more articular processes 20, 22. In some embodiments, the demineralized bone matrix 600 can span the facet joint 28. The demineralized bone matrix 600 can abut one or more articular processes 20, 22.

In some embodiments, the demineralized bone matrix 600 is delivered through a cannula or syringe to the facet joint 28. The demineralized bone matrix 600 can be a fluid and/or at least partially flowable through a cannula. The demineralized bone matrix 600 can be injected to the facet joint 28 and/or spread over the articular processes 20, 22 to form a cover over the superior articular process 20 and/or the inferior articular process 22. The cover can harden over time or with the use of a catalyst to form a rigid structure that stabilizes the facet joint 28. Advantageously, the demineralized bone matrix 600 can conform to the shape of the patient's articular processes 20, 22 and adhere to the bone for strong osseointegration.

In some embodiments, the demineralized bone matrix 600 is shaped to match the contour of the patient's anatomy. In some embodiments, the demineralized bone matrix 600 can be shaped based upon the anatomical shape of the articular processes 20, 22. The demineralized bone matrix 600 can have a generally flat configuration, curved configuration or combination thereof. For instance, a portion configured to be positioned near the superior articular process 20 is flat or substantially flat. For instance, a portion configured to be positioned near the inferior articular process 22 is curved or substantially curved. The demineralized bone matrix 600 can be concave or convex. In some embodiments, a portion of the demineralized bone matrix 600 is flat or concave and another portion of the demineralized bone matrix 600 is convex. Each surface of the demineralized bone matrix 600 need not have the same configuration. For instance, the bone facing surface of the demineralized bone matrix 600 can match or substantially match the anatomical shape of the articular processes 20, 22. The access surface of the demineralized bone matrix 600 can have the same shape or a different shape as the bone facing surface. The access surface of the demineralized bone matrix 600 can be flat while the bone facing surface of the demineralized bone matrix 600 is curved. The edges of the demineralized bone matrix 600 can optionally be rounded.

The demineralized bone matrix 600 can be substantially elongate or plate-like. The demineralized bone matrix 600 can have any cross-sectional shape, e.g., square, rectangular, polygonal, elliptical, circular, triangular, etc. The demineralized bone matrix 600 can have any of a variety of overall three dimensional shapes, including but not limited to a cube, cylinder, sphere, cone, cuboid, prism, etc. The demineralized bone matrix 600 can include one or more lumens or other apertures within the demineralized bone matrix 600. In some embodiments, the demineralized bone matrix 600 having the desired shape is selected from an array of demineralized bone matrixes 600 after radiographic visualization of the articular processes and/or by radio-contract injection into the facet joint to visualize the joint capsule.

In some embodiments, the average thickness of the demineralized bone matrix 600 can be within the range of about 1 mm to about 5 mm. In other embodiments, the average thickness of the demineralized bone matrix 600 can be within the range of about 1.5 mm to about 3.0 mm. The thicknesses of the demineralized bone matrix 600 need not to be uniform. For instance, a central portion of the demineralized bone matrix 600 overlying the facet joint 28 can be greater. In other embodiments, the lateral edges of the demineralized bone matrix 600 can have a greater thickness.

The demineralized bone matrix 600 can be formed from natural or artificial bone matrix and/or other osteogenesis factors. The demineralized bone matrix 600 can be positioned against the superior articular process 20, inferior articular process 22 or both the superior and inferior articular processes 20, 22. The demineralized bone matrix 600 can be attached with one or more fixation devices as described herein. In other embodiments, the demineralized bone matrix 600 can be attached using one or more absorbable fasteners.

H. Implantation Procedure

As shown in FIG. 7, the implant 100 can be used to stabilize adjacent vertebrae via the inferior articular process 22 of a first vertebra V1 and the superior articular process 20 of a second vertebra V2. In some embodiments, vertebra V1 and vertebra V2 are stabilized using only one implant 100 placed in one facet joint (e.g., the right facet joint). In some embodiments, one implant 100 can be used to stabilize vertebra V1 and vertebra V2 via the inferior articular process IAP1A of vertebra V1 and the superior articular process SAP2A of vertebra V2, or, via the inferior articular process IAP1B of vertebra V1 and the superior articular process SAP2B of vertebra V2. In others embodiments, vertebra V1 and vertebra V2 are stabilized using two implants 100, one placed in each facet joint (e.g., both the right and left facet joint). In some such embodiments, one implant 100 can be used to stabilize vertebra V1 and vertebra V2 via the inferior articular process IAP1A of vertebra V1 and the superior articular process SAP2A of vertebra V2, and another implant 100 can be used to stabilize vertebra V1 and vertebra V2 via the inferior articular process IAP1B of vertebra V1 and the superior articular process SAP2B of vertebra V2. The implant 200, 400, 500 can be delivered in a similar manner as implant 100.

In some embodiments, one or more spacers 114 are placed in the facet joint 28. As described herein, the spacers 114 can include the posterior side 116, the superior surface 118, the inferior surface 120, and the lateral sides 122, 124, and the anterior side 126. Upon insertion, the anterior side 126 is inserted first into the facet joint 28. The spacer 114 is oriented such that the superior surface 118 is adjacent or abuts the superior articular process 20. The spacer 114 is oriented such that the inferior surface 120 is adjacent or abuts the inferior articular process 22. In some embodiments, the posterior side 116 is inserted into the facet joint 28. In other embodiments, the posterior side 116 protrudes from the facet joint 28. The spacers 214, 414, 514 can be positioned in a similar manner as the spacer 114.

In some embodiments, the hinge joint 128 is assembled after the spacer 114 is inserted or partially inserted into the facet joint 28. In other embodiments, the hinge joint 128 is assembled prior to the spacer 114 being inserted into the facet joint 28. In some embodiments, the pivot 130 protrudes from the facet joint 28. The pivot 130 can be aligned with the axis of the facet joint 28. In some embodiments, the pivot 130 is positioned between the articular processes 20, 22. In some embodiments, the pivot is positioned within the facet joint 28. The implantation and assembly of the implant 200, 400, 500 can be similar to the method described with respect to implant 100.

Prior to use of the implant 100, a patient can be prepared for surgery. In some embodiments, the surgical procedure can include direct visualization of the facet joint 28 to be stabilized. Said another way, the medical practitioner can perform the operation without the use of fluoroscopy, and, in this manner, may not have to rely on the inaccuracies and/or inconvenience inherent in fluoroscopic procedures. This direct visualization can be possible due to the small incision necessary for implantation of the implant 100, for example, less than about the thickness of the fixation plate 102, and due to the ease of implanting and deploying the implant 100.

In some embodiments, the surgical procedure used can include forming an opening in body tissue substantially equidistant between the superior articular process 20 and the inferior articular process 22. A cannula (not shown) can be inserted through the opening and a proximal end of the cannula can be positioned near the articular processes 20, 22. A reamer or other device can be used to prepare the facet joint 28. The spacer 114 can be positioned within the cannula and can be advanced through the cannula until the anterior side 126 is positioned near the facet joint 28. The anterior side 126 can be inserted into the facet joint 28 until the spacer 114 is positioned within the facet joint 28. In some embodiments, the fixation plate 102 is delivered to the implantation site uncoupled from the spacer 114. In some embodiments, the fixation plate 102 remains a separate component form the spacer 110 such as shown in FIGS. 8A and 8B. In other embodiments, the fixation plate 102 is coupled to the spacer 114 after delivery to the implantation site, within the body of the patient. The hinge joint 128 can be designed for easy of assembly. For instance, the barrels 132 could snap onto the pivot 130.

In other embodiments, the fixation plate 102 is delivered to the implantation site coupled to the spacer (e.g., via the hinge joint). The fixation plate 102 can be oriented within the cannula to have a low profile configuration. In some embodiments, the fixation plate 102 can assume a low profile configuration during insertion. For instance, one or more portions of the fixation plate 102 can be pivoted about the hinge joint 128. In some embodiments, one or more portions can be parallel or substantially parallel to the superior surface 118 of the implant 114. In some embodiments, one or more portions can be parallel or substantially parallel to the inferior surface 120 of the implant 114. In some embodiments, one or more portions can be parallel or substantially parallel to the lateral sides 122, 124. The implants 200, 400, 500 can be delivered in a low profile configuration similar to the method described with respect to implant 100.

After delivery to the implantation site, the fixation plate 102 can be pivoted about the hinge joint 128 to assume a second configuration. In some embodiments, the upper portion 104 can be pivoted to be perpendicular or generally perpendicular to the superior surface 118. In some embodiments, the upper portion 104 can be pivoted to a position wherein at least a portion abuts or lie against the superior articular process 20. In some embodiments, the lower portion 106 can be pivoted to be perpendicular or generally perpendicular to the inferior surface 120. In some embodiments, the lower portion 106 can be pivoted to a position wherein at least a portion abuts or lie against the inferior articular process 22. The range of motion of the hinge joint 128 can be designed to allow the fixation plate 102 to substantially match or match the contour of the anatomy in the second configuration. The implants 200, 400, 500 pivoted to a second configuration similar to the method described with respect to implant 100.

The various embodiments described herein can enable the implant 100, 200, 400, 500 to closely conform to the patient's anatomy. For instance, the fixation plates described herein may be curved to match the anatomy of the facet joint 28. For instance, the implants described herein may include an intra-component hinges, separate plates, additional barrels or pivots. In some embodiments, the implants described herein may include multiple axes of rotation. In some embodiments, the movement joints described herein can have multiple degrees of movement.

In some embodiments, the fixation plates described herein includes one or more holes. During installation, one or more fixation devices can be inserted through one or more holes. The fixation devices can secure the fixation plates to the articular processes 20, 22. In some methods of use, a fixation device is inserted through a hole in the fixation plate into the superior articular process 20. In some methods of use, a fixation device is inserted through a hole in the fixation plate into the inferior articular process 22. In some methods of use, two or more fixation devices are inserted into each articular process. In some methods of use, one or more fixation devices are angled away from the spacer 114, 214, 414, 514. In some methods of use, one or more fixation devices are angled toward the spacer, 214, 414, 514.

In some embodiments, the patient can be intubated and general anesthesia can be achieved. The patient can be prepped and draped in the usual sterile fashion. A posterior approach to the spine can be used to expose the articular processes 20, 22. Many posterior approaches to the vertebral column are described in various medical texts such as Campbell's Operative Orthopaedics, 10th ed., edited by Canale et al., herein incorporated by reference. In some embodiments, the upper cervical spine can be accessed. In other embodiments, the lower cervical spine, cervicothoracic junction, thoracic spine, thoracolumbar junction, lumbar region, lumbosacral junction, sacrum or combination of the above regions can be accessed.

The facet joint 28 can be debrided. In some embodiments, the spacers described herein can be packed with natural or artificial bone matrix and/or other osteogenesis factors and inserted into the facet joint 28. The fixation plates described herein can be positioned against the superior and inferior articular processes 20, 22. The fixation plates described herein can be secured to the articular processes 20, 22. In some embodiments, one or more screws or anchors are passed through the holes in the fixation plates. The operative site can be irrigated with antibiotics and the operative field can be sutured closed. In some methods, the vertebral column can be accessed and one or more additional facet joints 28 can be identified and accessed. In some embodiments, two or more facet joints can be accessed, and in still other embodiments, two or more adjacent facet joints can be accessed. The operative site can be rinsed with antibiotic solution and the operative field can be closed in layers.

In another embodiment, a method for treating a spine can comprise the steps of providing an implant for treating the spine comprising two or more fixation plates, a spacer, and two or more articulation between the spacer and the two or more fixation plates, wherein the fixation plates are independently movable. The spacer can be inserted into a facet joint between a superior articular process of a first vertebra and an inferior articular process of a second vertebra. One of the fixation plates can be positioned to lie against the superior articular process of the first vertebra. The first fixation plate can be attached to the superior articular process of the first vertebra. A second fixation plate can be positioned in generally the opposite direction as the first fixation plate to lie against the inferior articular process of the second vertebra. The second fixation plate can be attached to the inferior articular process of the second vertebra. Any remaining fixation plates can further be positioned to lie against the superior and inferior articular processes or other portion of the spine and attached thereto.

In some embodiments, the method for treating a spine can further comprise providing a second implant for treating the spine comprising two or more fixation plates, a spacer, and two or more articulations between the spacer and the two or more fixation plates, wherein the fixation plates are independently movable. The spacer of the second implant can be inserted into a facet joint between a superior articular process of the first vertebra and an inferior articular process of the second vertebra. One of the fixation plates of the second implant can be positioned to lie against the superior articular process of the first vertebra. The first fixation plate of the second implant can be attached to the superior articular process of the first vertebra. A second fixation plate of the second implant can be positioned in generally the opposite direction as the first fixation plate to lie against the inferior articular process of the second vertebra. The second fixation plate of the second implant can be attached to the inferior articular process of the second vertebra. Any remaining fixation plates of the second implant can further be positioned to lie against the superior and inferior articular processes or other portion of the spine and attached thereto.

I. Conclusion

Although the present invention has been described in relation to various exemplary embodiments, various additional embodiments and alterations to the described embodiments are contemplated within the scope of the invention. Thus, no part of the foregoing description should be interpreted to limit the scope of the invention as set forth in the following claims. For all of the embodiments described above, the steps of the methods need not be performed sequentially.

What is claimed is:

1. An implant for treating a facet joint, comprising:
    a first fixation plate having an access surface and a bone facing surface, the first fixation plate configured to be outside of the joint space of the facet joint;
    a second fixation plate having an access surface and a bone facing surface, the second fixation plate configured to be outside of the joint space of the facet joint;
    a spacer comprising a single, unitary prosthesis configured to be inserted into the joint space of the facet joint comprising a first vertebra and a second vertebra, wherein the spacer comprises a circular disc comprising a superior surface and an inferior surface and at least one aperture extending from the superior surface to the inferior surface, wherein the superior surface is convex and the inferior surface is concave, wherein the superior surface is configured to contact the first vertebra and the inferior surface is configured to contact the second vertebra;
    at least one hinge between the single, unitary prosthesis of the spacer and the bone facing surfaces of the first fixation plate and the second fixation plate, wherein the first fixation plate and the second fixation plate are coupled to the single, unitary prosthesis, wherein the first fixation plate and the second fixation plate are configured to rotate about an axis, wherein the first fixation plate and the second fixation plate are positioned side by side on the axis; and
    demineralized bone matrix placed against the bone facing surfaces of the first fixation plate and the second fixation plate such that the demineralized bone matrix is configured to cover over at least a portion of an outer surface of a superior articular process and an inferior articular process, outside of the facet joint.
2. The implant of claim 1, wherein the first fixation plate has a plurality of holes.
3. The implant of claim 1, wherein the at least one hinge provides for pivoting articulation and movement between the spacer and the fixation plates.
4. The implant of claim 1, wherein the first fixation plate comprises an upper portion comprising at least one hole configured to accept a fixation device therethrough.
5. The implant of claim 4, wherein the second fixation plate comprises a lower portion comprising at least one hole configured to accept a fixation device therethrough.
6. The implant of claim 1, wherein the at least one hinge comprises a pair of hinges.
7. The implant of claim 1, wherein the implant comprises a low profile configuration wherein the first fixation plate is substantially parallel to the spacer.
8. The implant of claim 7, wherein the first fixation plate is configured to rotate to a second configuration wherein the first fixation plate is substantially perpendicular to the spacer.
9. The implant of claim 1, wherein the range of motion of each fixation plate is greater than 270 degrees.
10. The implant of claim 1, wherein the range of motion of each fixation plate is greater than 180 degrees.
11. A method for treating a spine, comprising:
    providing an implant comprising a fixation system having an access surface and a bone facing surface, and a spacer comprising a circular disc comprising a superior surface and an inferior surface and at least one aperture extending from the superior surface to the inferior surface, wherein at least one of the superior surface and the inferior surface is concave, and at least one hinge between the circular disc of the spacer and the bone facing surface of the fixation system, wherein the fixation system is coupled to the circular disc, wherein the fixation system comprises a first portion and a second portion, the first portion and the second portion configured to rotate about an axis, wherein the first portion rotates about a right portion of the axis and the second portion rotates about a left portion of the axis;
    inserting the spacer into a facet joint between a superior articular process of a first vertebra and an inferior articular process of a second vertebra to position the superior surface adjacent to the first vertebra and the inferior surface adjacent to the second vertebra;
    delivering demineralized bone matrix to form a cover over at least a portion of the outer surface of the superior articular process and the inferior articular process, outside of the facet joint, wherein delivering demineralized bone matrix to form the cover over the outer surface of the superior articular process and the inferior articular process further comprises placing the demineralized bone matrix between the fixation system and one or more articular processes; and
    attaching the first portion of the fixation system to the first vertebra and attaching the second portion of the fixation system to the second vertebra.
12. The method of claim 11, wherein attaching the fixation system to the first vertebra and the second vertebra comprises attaching a first fixation plate to the first vertebra and attaching a second fixation plate to the second vertebra.
13. The method of claim 11, wherein the spacer is sized to fit within the joint capsule of the facet joint.
14. The method of claim 11, wherein the at least one aperture is filled with graft material.
15. The method of claim 11, further comprising rotating the first portion of the fixation system greater than 180 degrees.
16. A method for treating a facet joint comprising a superior articular process and an inferior articular process, comprising:
    implanting a spacer into the joint space of the facet joint and between the superior articular process and the inferior articular process, without securing the spacer to any bony structure, wherein the spacer is a circular disc comprising at least one aperture extending from a superior surface to an inferior surface; and
    delivering demineralized bone matrix to form a cover over the spacer and at least a portion of the outer surface of the superior articular process and the inferior articular process, outside of the facet joint, wherein delivering demineralized bone matrix to form the cover over the outer surface of the superior articular process and the inferior articular process further comprises placing the demineralized bone matrix between a fixation plate and one or more articular processes.

17. The method of claim 16, wherein the demineralized bone matrix is at least partially flowable through a cannula.

18. The method of claim 16, wherein the demineralized bone matrix is shaped to match the contour of the superior articular process and an inferior articular process.

19. The method of claim 16, wherein the at least one aperture is filled with graft material.

* * * * *